United States Patent
Altaf et al.

(10) Patent No.: US 9,840,528 B2
(45) Date of Patent: *Dec. 12, 2017

(54) THIONE-PLATINUM(II) COMPLEXES AND PHARMACEUTICAL COMPOSITIONS THEREOF

(71) Applicant: KING FAHD UNIVERSITY OF PETROLEUM AND MINERALS, Dhahran (SA)

(72) Inventors: Muhammad Altaf, Dhahran (SA); Anvarhusein Abdulkadir Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/282,014

(22) Filed: Sep. 30, 2016

(65) Prior Publication Data

US 2017/0073363 A1    Mar. 16, 2017

Related U.S. Application Data

(63) Continuation of application No. 14/854,225, filed on Sep. 15, 2015, now Pat. No. 9,481,699.

(51) Int. Cl.
| | | |
|---|---|---|
| *A61K 31/55* | (2006.01) | |
| *A61K 31/505* | (2006.01) | |
| *A61K 31/415* | (2006.01) | |
| *C07D 243/00* | (2006.01) | |
| *C07D 403/00* | (2006.01) | |
| *C07D 233/00* | (2006.01) | |
| *C07F 15/00* | (2006.01) | |
| *A61K 31/555* | (2006.01) | |

(52) U.S. Cl.
CPC ........ *C07F 15/0093* (2013.01); *A61K 31/555* (2013.01)

(58) Field of Classification Search
None
See application file for complete search history.

(56) References Cited

PUBLICATIONS

Jianxin Lin, et al., "Synthesis and characterization of platinum(II) complexes with 2-imidazolidinethione. X-ray crystal structure of tetra(2-imidazolidinethione-S)platinum(II) iodide dimethylsulfoxide solvate monohydrate", Journal of Coordination Chemistry, vol. 61, No. 15, Aug. 10, 2008, pp. 2457-2469.

Jean-Michel Bret, et al., "NMR (195Pt and 13C) contribution to the study of some Pt (II), Pt(IV) and mixed-valence thioamido complexes", Polyhedron, vol. 2, No. 9, 1983, pp. 901-905 (Abstract only).

Jean-Michel Bret, et al., "Bromo Bridged Mixed-Valence Complexes of Platinum with Thioamido Ligands", Inorganica Chimica Acta, vol. 54, No. 5, 1981, pp. L237-L238.

Jean-Michel Bret, et al., "Coordination complexes of platinum(II) and platinum(II) with ligands involving the thioamido group: chloro bridged mixed-valence compounds", Inorganica Chimica Acta, vol. 51, No. 1, 1981, pp. 103-107 (Abstract only).

Paule Castan, et al., "Platinum(II) complexes with ligands involing the —NH—CS—NH-Group in heterocyclic rings", Transition Metal Chemistry, vol. 5, Issue 1, Dec. 1980, pp. 154-157 (Summary only).

Yu. N. Kukushkin, et al., "Complexes of platinum(II) with thiourea derivatives", Zhurnal Obshchei Khimii, vol. 47, No. 6, 1977, pp. 1402-1408 (Abstract only).

Wisniewski et al. Archivum Immunologiae et Therapiae Experimentalis (2000), 48(1), 51-55.

*Primary Examiner* — Jeffrey S Lundgren
*Assistant Examiner* — Michael Schmitt
(74) *Attorney, Agent, or Firm* — Oblon, McClelland, Maier & Neustadt, L.L.P.

(57) ABSTRACT

Platinum(II) complexes having thione-based heterocyclic ligands as anticancer agents. The central platinum atom is coordinated by four of the ligands, each having a five-, six- or seven-membered heterocyclic ring with two nitrogen atoms at positions 1 and 3 of the ring and a thiocarbonyl group at position 2. Pharmaceutical compositions incorporated the platinum(II) complexes, methods of synthesizing the complexes and methods of treating cancers with the complexes or pharmaceutical compositions thereof are also described.

7 Claims, 6 Drawing Sheets

THIONE-PLATINUM(II) COMPLEXES AND PHARMACEUTICAL COMPOSITIONS THEREOF

CROSS-REFERENCE TO RELATED APPLICATIONS

This application is a continuation of Ser. No. 14/854,225, allowed.

BACKGROUND OF THE INVENTION

Technical Field

The present invention relates to pharmaceutical compounds. More specifically, the present invention relates to platinum(II) complexes having thione ligands. The present invention includes the use of these platinum(II) complexes for treatment of cancers and cell proliferative disorders.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Since the discovery of the platinum-based drug cisplatin, its clinical use has been reduced by its severe side effects such as nephrotoxicity and gastrointestinal effects, and also by the resistance of cancer cells to the drug [B. Rosenberg, L. VanCamp, and T. Krigas, Nature, 205 (1965) 698; M. Goren, R. Wright, and M. Horowitz, Cancer Chemoth. Pharm., 18 (1986) 69; L. R. Kelland, G. Abel, M. J. McKeage, M. Jones, P. M. Goddard, M. Valenti. B. A. Murrer, and K. R. Harrap, Cancer Res., 53 (1993) 2581—each incorporated herein by reference in its entirety]. As a result, several alternative platinum complexes have been synthesized in order to overcome these side effects. Platinum (II) complexes that have the classical structure cis-[PtX$_2$(NHR$_2$)$_2$], in which X=leaving group and R=organic fragment, are found to bind to the DNA through 1,2-intrastrand cross-links, between N7 atoms of two adjacent guanine (G) with platinum(II) ion [X. Wang and Z. Guo, Chem Soc Rev 42 (2013) 202; N. Muhammad and Z. Guo, Curr Opin Chem Biol 19 (2014) 144; J. S. Butler and P. J. Sadler, Curr Opin Chem Biol 17 (2013) 175—each incorporated herein by reference in its entirety].

The search for a new generation of platinum(II) complexes, which are able to broaden the biological activity spectrum and eliminate the multifactorial drug resistance, resulted in the synthesis of structurally novel platinum(II) complexes containing biologically active ligands. These complexes are supposed to interact with the DNA through a mechanism different from that of cisplatin. Studies found that cisplatin-like drugs could introduce nephrotoxicity due to their reaction with sulfur-containing amino acids of the proteins: cysteine and methionine [J. S. Butler and P. J. Sadler, Curr Opin Chem Biol 17 (2013) 175—incorporated herein by reference in its entirety]. Platinum(I) complexes with sulfur-containing ligands, like dimethyl sulfoxide, dimethyl sulfide, xanthate and thiosemicarbazones have already shown high efficacy against some human cancer cell lines [A. Muscella, N. Calabriso, S. A. De Pascali, L. Urso, A. Ciccarese, F. P. Fanizzi, D. Migoni, and S. Marsigliante, Biochem. Pharm., 74 (2007) 28; W. Friebolin, G. Schilling, M. Zöller, and E. Amtmann, J. Med. Chem., 47 (2004) 2256; A. A. Ali, H. Nimir, C. Aktas, V. Huch, U. Rauch, K.-H. Schäfer, and M. Veith, Organometallics, 31 (2012) 2256—each incorporated herein by reference in its entirety].

Thiourea and its derivatives as sulfur-containing ligands are expected to give better results if they coordinate with the platinum(II) ion. They have been routinely used as antifungal agents, rescue agents against nephritic side effects during cisplatin administration, and as inhibitors of HIV-1 and HIV-2 reverse transcriptases [R. del Campo, J. J. Criado, E. Garcia. M. a. R. Hermosa, A. Jiménez-Sánchez, J. L. Manzano, E. Monte. E. Rodríguez-Fernández, and F. Sanz, J. Biol. Inorg. Chem., 89 (2002) 74; J. Ren, J. Diprose, J. Warren. R. M. Esnouf, L. E. Bird, S. Ikemizu. M. Slater, J. Milton. J. Balzarini, D. I. Stuart, and D. K. Stammers, J. Biol. Chem., 275 (2000) 5633—each incorporated herein by reference in its entirety]. Platinum(II) complexes with thiourea ligands demonstrated that they can bind to the DNA in a different mechanism to that of cisplatin and showed excellent cytotoxicity against ovarian and leukemia cancer cell lines [Z. Ma, L. Rao, and U. Bierbach, J. Med. Chem., 52 (2009) 3424; J. M. Brow, C. R. Pleatman, and U. Bierbach, Bioorg. Med. Chem. Lett., 12 (2002) 2953—each incorporated herein by reference in its entirety].

New platinum(II) complexes with thiourea derivatives were synthesized and characterized in order to provide compounds having improved treatment activity for cancers and cell proliferative disorders.

BRIEF SUMMARY OF THE INVENTION

According to a first aspect, the present disclosure provides a platinum(II) complex of Formula I, Formula II or Formula III:

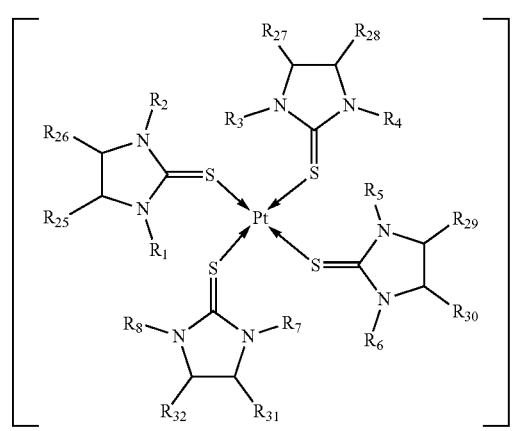

Formula I

-continued

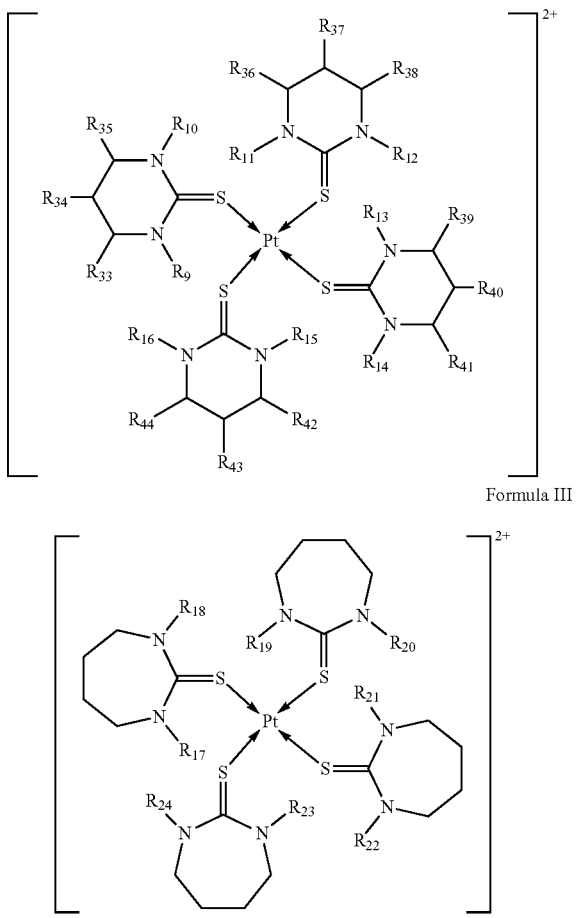

Formula II

Formula III or a pharmaceutically acceptable salt, tautomer, ester, solvate or prodrug thereof. $R_1$, $R_3$, $R_5$, $R_7$, $R_9$, $R_{11}$, $R_{13}$ and $R_{15}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group when $R_2$, $R_4$, $R_6$, $R_8$, $R_{10}$, $R_{12}$, $R_{14}$ and $R_{16}$ are each independently a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group. Alternately, $R_1$, $R_3$, $R_5$, $R_7$, $R_9$, $R_{11}$, $R_{13}$ and $R_{15}$ are each independently a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group when $R_2$, $R_4$, $R_6$, $R_8$, $R_{10}$, $R_{12}$, $R_{14}$ and $R_{16}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group. $R_{17}$-$R_{24}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group.

In one embodiment, $R_1$, $R_3$, $R_5$, $R_7$, $R_9$, $R_{11}$, $R_{13}$ and $R_{15}$ are each independently a hydrogen atom, a methyl group, an ethyl group, a propyl group or an isopropyl group when $R_2$, $R_4$, $R_6$, $R_8$, $R_{10}$, $R_{12}$, $R_{14}$ and $R_{16}$ are each independently a methyl group, an ethyl group, a propyl group or an isopropyl group. Alternatively, $R_1$, $R_3$, $R_5$, $R_7$, $R_9$, $R_{11}$, $R_{13}$ and $R_{15}$ are each independently a methyl group, an ethyl group, a propyl group or an isopropyl group when $R_2$, $R_4$, $R_6$, $R_8$, $R_{10}$, $R_{11}$, $R_2$, $R_{14}$ and $R_{16}$ are each independently a hydrogen atom, a methyl group, an ethyl group, a propyl group or an isopropyl group. $R_{17}$-$R_{24}$ are each independently a hydrogen atom, a methyl group, an ethyl group, a propyl group or an isopropyl group.

In one embodiment, $R_1$, $R_3$, $R_5$, $R_7$, $R_9$, $R_{11}$, $R_{13}$ and $R_{15}$ are each a hydrogen atom when $R_2$, $R_4$, $R_6$, $R_8$, $R_{10}$, $R_{12}$, $R_{14}$ and $R_{16}$ are each a methyl group, an ethyl group, a propyl group or an isopropyl group. Alternately, $R_1$, $R_3$, $R_5$, $R_7$, $R_9$, $R_{11}$, $R_{13}$ and $R_{15}$ are each a methyl group, an ethyl group, a propyl group or an isopropyl group when $R_2$, $R_4$, $R_6$, $R_8$, $R_{10}$, $R_{12}$, $R_{14}$ and $R_{16}$ are each a hydrogen atom. $R_{17}$-$R_{24}$ are each a hydrogen atom. $R_{25}$-$R_{60}$ are each independently a hydrogen atom, a halogen atom, an optionally substituted $C_1$-$C_8$ alkyl group, an optionally substituted $C_1$-$C_8$ alkoxy group, an optionally substituted $C_2$-$C_8$ alkenyl group or an optionally substituted $C_2$-$C_8$ alkynyl group.

According to a second aspect, the present disclosure relates to a pharmaceutical composition incorporating the platinum(II) complex and one or more pharmaceutically acceptable carriers, other active pharmaceutical agents, non-active ingredients. The pharmaceutical composition, which can exist in solid, semi-solid or liquid dosage forms, is formulated for multiple modes of administration.

According to a third aspect, the present disclosure provides a method for cancer treatment using the pharmaceutical composition incorporating the platinum(II) complex.

According to a fourth aspect, the present disclosure provide a method for inducing apoptosis in a cancer cell by contacting the cancer cell with the platinum(II) complex.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
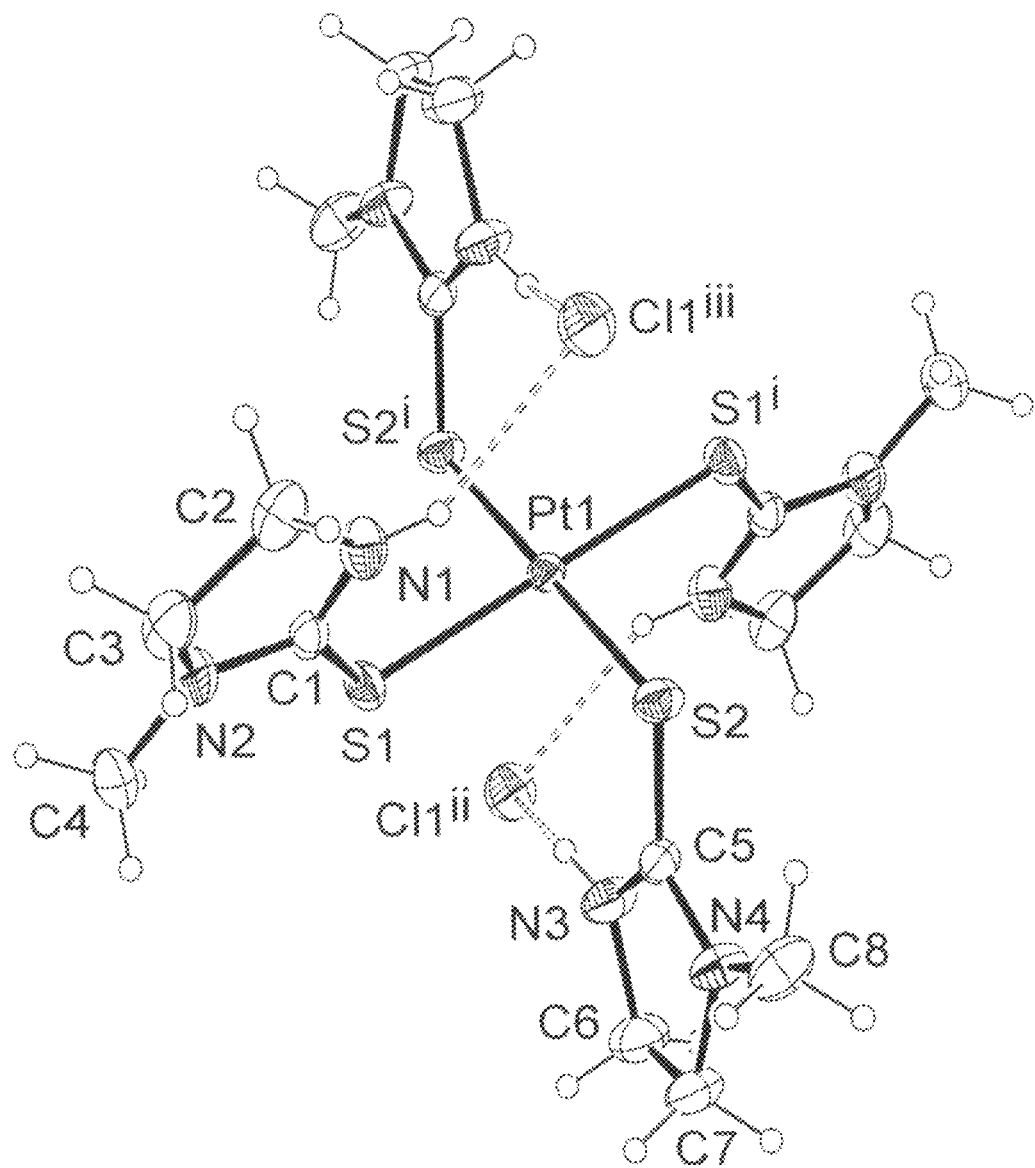
FIG. 1 is an ORTEP diagram of Complex (1), showing the molecular structure of complex (1) obtained by X-ray diffraction and the atomic labeling scheme.

Referring now to the drawings, wherein like reference numerals designate identical or corresponding parts throughout the several views.

The present disclosure will be better understood with reference to the following definitions:

As used herein, "compound" and "complex" are used interchangeably, and are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically $C_1$ to $C_8$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, thioalkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis". John Wiley and Sons, Second Edition, 1991, hereby incorporated by reference in its entirety.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_{12}$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-ethenyl)-pentenyl. An alkenyl group can be unsubstituted or substituted with one or more suitable substituents.

The term "alkynyl" means a monovalent, unbranched or branched hydrocarbon chain having one or more triple bonds therein. The triple bond of an alkynyl group can be unconjugated or conjugated to another unsaturated group. Suitable alkynyl groups include, but are not limited to ($C_2$-$C_{12}$)alkynyl groups, such as ethynyl, propynyl, butyryl, pentynyl, hexynyl, 2-ethylhexynyl, 2-propyl-2-butyryl, 4-(2-methyl-3-ethynyl)-pentynyl. An alkynyl group can be unsubstituted or substituted with one or more suitable substituents.

When a substituent is noted as "optionally substituted", the substituents are selected from, for example, substituents, such as, halo, hydroxy, alkoxy, oxo, alkanoyl, alkanoyloxy, amino, alkylamino, disubstituted amines in which the 2 amino substituents are alkyl; alkanoylamino, substituted alkanoylaminothiol, alkylthio, alkylthiono, alkylsulfonyl, arylsulfonyl, sulfonamido, e.g., —$SO_2NH_2$, substituted sulfonamido, nitro, cyano, carboxy, carbamyl, e.g., —$CONH_2$, substituted carbamyl e.g., —CONHalkyl, —CONHaryl, —CONHarylalkyl or cases where there are two substituents on the nitrogen selected from alkyl; alkoxycarbonyl, guanidine, and the like.

As used herein, "analogue" refers to a chemical compound that is structurally similar to a parent compound, but differs slightly in composition (e.g., one atom or functional group is different, added, or removed). The analogue may or may not have different chemical or physical properties than the original compound and may or may not have improved biological and/or chemical activity. For example, the analogue may be more hydrophilic or it may have altered reactivity as compared to the parent compound. The analogue may mimic the chemical and/or biologically activity of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis [Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics. *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000)). Improving Oral Drug Transport Via Prodrugs, in G. L. Amidon, P. I. Lee and E. M. Topp. Eds., Transport Processes in Pharmaceutical Systems, Marcell Dekker, p. 185-218; Balant et al. (1990) Prodrugs for the improvement of drug absorption via different routes of administration, *Eur. J. Drug Metab. Pharmacokinet.*, 15(2):

143-53; Balimane and Sinko (1999). Involvement of multiple transporters in the oral absorption of nucleoside analogues, *Adv. Drug Delivery Rev.,* 39 (1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 8611): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Method Enzymol.* 112: 360-81; Farquhar D, et al. (1983). Biologically Reversible Phosphate-Protective Groups, *J. Pharm. Sci.,* 72(3): 324-325; Han. H. K. et al. (2000). Targeted prodrug design to optimize drug delivery, *AAPS PharmSci.,* 2(1): E6; Sadzuka Y. (2000). Effective prodrug liposome and conversion to active metabolite, *Curr. Drug Metab.,* 1(1):31-48; D. M. Lambert (2000) Rationale and applications of lipids as prodrug carriers, *Eur. J. Pharm. Sci.,* 11 Suppl 2:S15-27; Wang, W. et al. (1999) Prodrug approaches to the improved delivery of peptide drugs. *Curr. Pharm. Des.,* 5(4):265-87—each incorporated herein by reference in its entirety]. In some embodiments, "Pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "tautomer", as used herein, refers to a constitutional isomer of a compound of this disclosure, specifically the one or more thione-based heterocyclic ligands coordinated to the platinum core atom, that readily interconvert between a thione form having a saturated heterocyclic ring and a thiol form having a non-saturated heterocyclic ring by a chemical reaction called tautomerization. The tautomerization chemical reaction results in the formal migration of a hydrogen atom or proton, which is accompanied by a switch of a single bond and an adjacent double bond in a thiocarbonyl group or in the heterocyclic ring. It should be understood that all tautomeric forms, which share the same molecular formula and insofar as they may exist, are included within the invention. It should also be appreciated that these tautomers can exist in equilibrium.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor. (2) inhibiting (that is, slowing to some extent, preferably stopping) aberrant cell division, growth or proliferation, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment." and "treating" in the context of the administration of a therapy to a subject in need thereof refer to the reduction or inhibition of the progression and/or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population: (2) a stabilization, reduction or elimination in the cancer cell population; (3) a stabilization or reduction in the growth of a tumor or neoplasm; (4) an impairment in the formation of a tumor: (5) eradication, removal, or control of primary, regional and/or metastatic cancer: (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the pharmaceutical composition refers to the combination of an active agent with a carrier, inert or active, making the composition especially suitable for diagnostic or therapeutic use in vivo or ex vivo.

"Pharmaceutically acceptable salt" or "pharmaceutically acceptable ester" refers to a compound in a pharmaceutically acceptable form such as an ester, a phosphate ester, a salt of an ester or a related) which, upon administration to a subject in need thereof, provides at least one of the platinum(II) complexes described herein. Pharmaceutically acceptable salts and ester retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, alkaline earth metals such as calcium and magnesium, among numerous other acids well known in the art.

A "pharmaceutical composition" refers to a mixture of the compounds described herein or pharmaceutically acceptable salts, esters or prodrugs thereof, with other chemical components, such as physiologically and pharmaceutically acceptable carriers, diluents and excipients. One purpose of a pharmaceutical composition is to facilitate administration of at least one platinum(II) complex to a subject.

As used herein, a "pharmaceutically acceptable carrier" or "pharmaceutically acceptable excipient" refers to a carrier or diluent that does not cause significant irritation to an organism and does not abrogate the biological activity and properties of the administered platinum(II) complex. The term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott. Williams & Wilkins, Philadelphia Pa., 2005, which is incorporated herein by reference in its entirety. Examples of pharmaceutically acceptable carriers include (1) sugars, such as lactose, glucose and sucrose; (2) starches, such as corn starch and potato starch: (3) cellulose, and its derivatives, such as sodium carboxymethyl cellulose, ethyl cellulose and cellulose acetate; (4) powdered tragacanth: (5) malt: (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol: (11) polyols, such as glycerin, sorbitol, mannitol and polyethylene glycol; (12) esters, such as ethyl oleate and ethyl laurate; (13) agar: (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like: and (3) metal chelating agents, such as citric acid, ethylenediamine tetraacetic acid (EDTA), sorbitol, tartaric acid, phosphoric acid, and the like.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol (2) proteins such as gelatin and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

The terms "including", "such as", "for example" and the like are intended to refer to exemplary embodiments and not to limit the scope of the present disclosure.

Platinum(II) Complexes and Pharmaceutical Compositions Thereof

The present disclosure provides platinum(II) complexes having medicinal or pharmaceutical properties, preferably antitumor, anticancer and/or antiproliferative properties. In these platinum(II) complexes, each central platinum(II) atom is coordinated, preferably chelated, by four ligands. Each ligand has a saturated five-, six- or seven-membered heterocyclic ring with two nitrogen atoms at positions 1 and 3 of the ring and a thiocarbonyl functional group at position 2. Specifically, each ligand is thione-based with an imidazolidine, tetrahydropyrimidine or 1,3-diazepane ring and their base, unsubstituted structures are shown as Formulas A-C below:

Formula A

imidazolidine-2-thione

Formula B

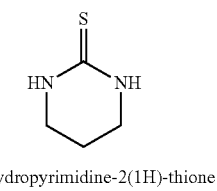

tetrahydropyrimidine-2(1H)-thione

Formula C

1,3-diazepane-2-thione

The thione-based ligands and derivatives thereof bind to the central platinum(II) atom in a monodentate manner, The sulfur atoms of the thiocarbonyl group act as electron donor atoms that the platinum(II) atom is coordinated by. In other words, the platinum(II) atom is coordinated to four donor sulfur atoms from four thione-based, heterocyclic ligands. Accordingly, a platinum(II) complex described herein has a generic structure of Formula I, Formula II or Formula III:

Formula I

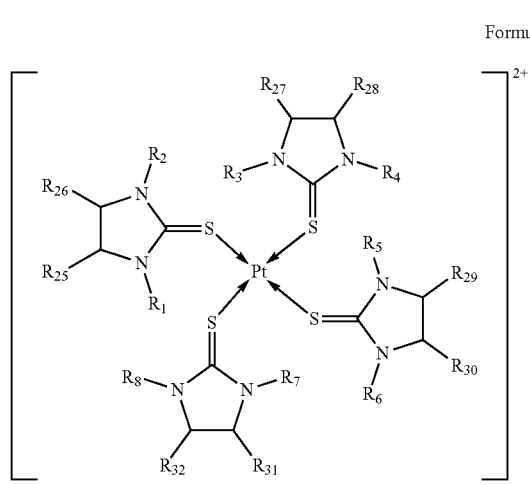

Formula II

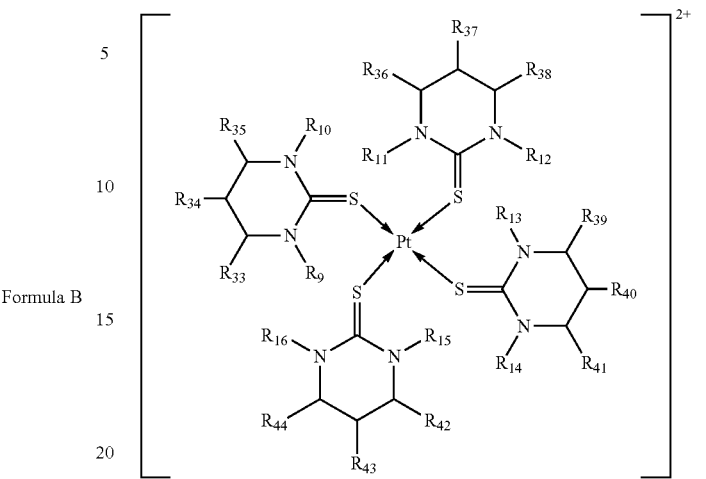

Formula III

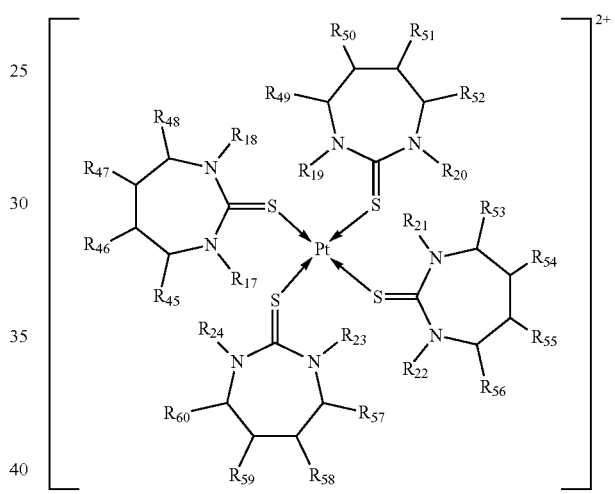

or a pharmaceutically acceptable salt, tautomer, ester, solvate or prodrug thereof; where:

$R_1$, $R_3$, $R_5$, $R_7$, $R_9$, $R_{11}$, $R_{13}$ and $R_{15}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group when $R_2$, $R_4$, $R_6$, $R_8$, $R_{10}$, $R_{12}$, $R_{14}$ and $R_{16}$ are each independently a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group; or $R_1$, $R_3$, $R_5$, $R_7$, $R_9$, $R_{11}$, $R_{13}$ and $R_{15}$ are each independently a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group when $R_2$, $R_4$, $R_6$, $R_8$, $R_{10}$, $R_{12}$, $R_{14}$ and $R_{16}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group;

$R_{17}$-$R_{24}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group; and $R_{25}$-$R_{60}$ are each independently a hydrogen atom, a halogen atom, an optionally substituted $C_1$-$C_8$ alkyl group, an optionally substituted $C_1$-$C_8$ alkoxy group, an optionally substituted $C_2$-$C_8$ alkenyl group or an optionally substituted $C_2$-$C_8$ alkynyl group.

Preferably, $R_1$, $R_3$, $R_5$, $R_7$, $R_9$, $R_{11}$, $R_{13}$ and $R_{15}$ are each independently a hydrogen atom, a methyl group ($CH_3$), an ethyl group ($C_2H_5$), a propyl group ($C_3H_7$) or an isopropyl group ($C_3H_7$) when $R_2$, $R_4$, $R_6$, $R_8$, $R_{10}$, $R_{12}$, $R_{14}$ and $R_{16}$ are each independently a methyl group, an ethyl group, a propyl group or an isopropyl group. Alternately, $R_1$, $R_3$, $R_5$, $R_7$, $R_9$, $R_{11}$, $R_{13}$ and $R_{15}$ are each independently a methyl group ($CH_3$), an ethyl group ($C_2H_5$), a propyl group ($C_3H_7$) or an isopropyl group ($C_3H_7$) when $R_2$, $R_4$, $R_6$, $R_5$, $R_{10}$, $R_{12}$, $R_{14}$ and $R_{16}$ are each independently a hydrogen atom, a methyl group, an ethyl group, a propyl group or an isopropyl group. $R_{17}$-$R_{24}$ are each independently a hydrogen atom, a methyl group, an ethyl group, a propyl group or an isopropyl group. $R_{25}$-$R_{60}$ are each a hydrogen atom.

More preferably, the four ligands coordinating the central platinum(II) atom are the same and the platinum(II) complex is one of the following:

Tetrakis(1-methylimidazolidine-2-thione)platinum(II);
Tetrakis(1-ethylimidazolidine-2-thione)platinum(II);
Tetrakis(1-propylimidazolidine-2-thione)platinum(II);
Tetrakis(1-isopropylimidazolidine-2-thione)platinum(II);
Tetrakis(1,3-dimethylimidazolidine-2-thione)platinum(II):
Tetrakis(1-ethyl-3-methylimidazolidine-2-thione)platinum (II);
Tetrakis(1-propyl-3-methyl imidazolidine-2-thione)platinum(II);
Tetrakis(1-isopropyl-3-methylimidazolidine-2-thione)platinum(II);
Tetrakis(1,3-diethylimidazolidine-2-thione)platinum(II);
Tetrakis(1-propyl-3-ethylimidazolidine-2-thione)platinum (II);
Tetrakis(1-isopropyl-3-ethylimidazolidine-2-thione)platinum(II);
Tetrakis(1,3-dipropylimidazolidine-2-thione)platinum(II);
Tetrakis(1-isopropyl-3-propylimidazolidine-2-thione)platinum(II);
Tetrakis(1,3-diisopropylimidazolidine-2-thione)platinum (II);
Tetrakis[1-methyltetrahydropyrimidine-2(1H)-thione]platinum(II);
Tetrakis[1-ethyltetrahydropyrimidine-2(1H)-thione]platinum(II);
Tetrakis[1-propyltetrahydropyrimidine-2(1H)-thione]platinum(II);
Tetrakis[1-isopropyltetrahydropyrimidine-2(1H)-thione] platinum(II);
Tetrakis[1,3-dimethyltetrahydropyrimidine-2(1H)-thione] platinum(II):
Tetrakis[1-ethyl-3-methyltetrahydropyrimidine-2(1H)-thione]platinum(II);
Tetrakis[1-propyl-3-methyltetrahydropyrimidine-2(1H)-thione]platinum(II);
Tetrakis[1-isopropyl-3-methyltetrahydropyrimidine-2(1H)-thione]platinum(II);
Tetrakis[1,3-diethyltetrahydropyrimidine-2(1H)-thione] platinum(II);
Tetrakis[1-propyl-3-ethyltetrahydropyrimidine-2(1H)-thione]platinum(II);
Tetrakis[1-isopropyl-3-ethyltetrahydropyrimidine-2(1H)-thione]platinum(II);
Tetrakis[1,3-dipropyltetrahydropyrimidine-2(1H)thione] platinum(II);
Tetrakis[1-isopropyl-3-propyltetrahydropyrimidine-2(1H)-thione]platinum(II);
Tetrakis[1,3-diisopropyltetrahydropyrimidine-2(1H)-thione]platinum(II);
Tetrakis(1,3-diazepane-2-thione)platinum(II);
Tetrakis(1-methyl-1,3-diazepane-2-thione)platinum(II);
Tetrakis(1-ethyl-1,3-diazepane-2-thione)platinum(II);
Tetrakis(1-propyl-1,3-diazepane-2-thione)platinum(II);
Tetrakis(1-isopropyl-1,3-diazepane-2-thione)platinum(II);
Tetrakis(1,3-dimethyl-1,3-diazepane-2-thione)platinum(II);
Tetrakis(1-ethyl-3-methyl-1,3-diazepane-2-thione)platinum (II);
Tetrakis(1-propyl-3-methyl-1,3-diazepane-2-thione)platinum(II);
Tetrakis(1-isopropyl-3-methyl-1,3-diazepane-2-thione) platinum(II);
Tetrakis(1,3-diethyl-1,3-diazepane-2-thione)platinum(II):
Tetrakis(1-propyl-3-ethyl-1,3-diazepane-2-thione)platinum (II);
Tetrakis(1-isopropyl-3-ethyl-1,3-diazepane-2-thione)platinum(II):
Tetrakis(1,3-dipropyl-1,3-diazepane-2-thione)platinum(II);
Tetrakis(1-isopropyl-3-propyl-1,3-diazepane-2-thione)platinum(II); and
Tetrakis(1,3-diisopropyl-1,3-diazepane-2-thione)platinum (II).

Even more preferably, $R_1$, $R_3$, $R_5$, $R_7$, $R_9$, $R_{11}$, $R_{13}$ and $R_{15}$ are each a hydrogen atom when $R_2$, $R_4$, $R_6$, $R_8$, $R_{10}$, $R_{12}$, $R_{14}$ and $R_{16}$ are each a methyl group, an ethyl group, a propyl group or an isopropyl group; or $R_1$, $R_3$, $R_5$, $R_7$, $R_9$, $R_{11}$, $R_{13}$ and $R_{15}$ are each a methyl group, an ethyl group, a propyl group or an isopropyl group when $R_2$, $R_4$, $R_6$, $R_8$, $R_{10}$, $R_{12}$, $R_{14}$ and $R_{16}$ are each a hydrogen atom; and $R_{17}$-$R_{60}$ are each a hydrogen atom. Accordingly, the platinum(II) complex is one the following:

Tetrakis(1-methylimidazolidine-2-thione)platinum(II);
Tetrakis(1-ethylimidazolidine-2-thione)platinum(II);
Tetrakis(1-propylimidazolidine-2-thione)platinum(II);
Tetrakis(1-isopropylimidazolidine-2-thione)platinum(II):
Tetrakis[1-ethyltetrahydropyrimidine-2(1H)-thione]platinum(II); and
Tetrakis(1,3-diazepane-2-thione)platinum(II).

In certain embodiments, especially but not limited to pharmaceutical applications, the platinum(II) complex can further include a counter-anion to form a pharmaceutically acceptable salt. As used herein, the term "counter-anion" refers to an anion, preferably a pharmaceutically acceptable anion that is associated with a positively charged platinum (II) complex of at least one of the Formulas 1-3. Non-limiting examples of pharmaceutically counter-anions include halides such as fluoride, chloride, bromide, iodide: nitrate; sulfate; phosphate; amide; methanesulfonate; ethanesulfonate; p-toluenesulfonate, salicylate, malate, maleate, succinate, tartarate; citrate; acetate; perchlorate: trifluoromethanesulfonate (triflate); acetylacetonate; hexafluorophosphate; and hexafluoroacetylacetonate. In some embodiments, the counter-anion is a halide (preferably chloride) or nitrate.

Another aspect of the present disclosure relates to pharmaceutical composition comprising one or more of the platinum(II) complexes described herein. In other words, the platinum(II) complexes described herein or analogues or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of one or more of the platinum(II) complexes described herein or derivatives thereof in combination with a pharmaceutically acceptable carrier and, in addition, may include other medicinal agents, pharmaceutical agents, carriers, diluents or other non-active ingredients. By pharmaceutically acceptable is meant a material that is not biologically or otherwise undesirable, which can be administered to an individual along with the selected compound without causing significant unacceptable biological effects or interacting in a deleterious manner with the other components of the pharmaceutical composition in which it is contained.

A platinum(II) complex of the present disclosure or an analogue or derivative thereof may be used in conjunction with one or more additional compounds, in the treatment or prevention of neoplasm: of tumor or cancer cell division, growth, proliferation and/or metastasis in a mammalian subject; induction of death or apoptosis of tumor and/or cancer cells; and/or any other form of proliferative disorder. A platinum(I) complex of the present disclosure can be formulated as a pharmaceutical composition.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system. The platinum(II) complex of the present disclosure or the pharmaceutical composition thereof is especially effective in the treatment or prevention of colorectal cancer (including colon cancer, rectum cancer and bowel cancer); lung cancer (including non-small cell lung carcinoma or NSCLC and small cell lung carcinoma); cervical cancer (including the histologic subtypes of squamous cell carcinoma, adenocarcinoma, adenosquamous carcinoma, small cell carcinoma, neuroendocrine tumor, glass cell carcinoma, villoglandular adenocarcinoma, melanoma and lymphoma).

A pharmaceutical composition comprising one or more platinum(II) complexes of the present disclosure can then be administered orally, systemically, parenterally, by inhalation spray, rectally, or topically in dosage unit formulations containing conventional nontoxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration such as transdermal patches or iontophoresis devices. The term parenteral as used herein includes intravesical, intradermal, transdermal, subcutaneous, intramuscular, intralesional, intracranial, intrapulmonal, intracardial, intrasternal and sublingual injections, or infusion techniques. Formulation of drugs is discussed in, for example. Hoover, John E., Remington's Pharmaceutical Sciences. Mack Publishing Co., Easton, Pa.; 1975. Another example of includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful. Suppositories for rectal administration of the compound or an analogue or derivative thereof can be prepared by mixing the steroid or an analogue or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredients that can be combined with the carrier materials to produce a single dosage form varies depending upon the mammalian subject treated and the particular mode of administration.

Methods of Synthesizing Platinum(II) Complexes

The platinum(II) complexes of the present disclosure are not limited by their synthesis routes and methods. These platinum(II) complexes can be prepared by various previously reported synthesis protocols with slight modifications as recognized as appropriate by a person of ordinary skill in the pharmaceutical and medicinal chemistry arts [A. Z. A. Mustafa, M. Altaf, M. Monim-ul-Mehboob, M. Fettouhi, M. I. M. Wazeer, A. A. Isab, V. Dhuna, G. Bhatia, K. Dhuna, Inorg. Chem. Commun., 44 (2014) 159; G. D. Thorn, Can. J. Chem., 33 (1955) 1278; L. Maier, Helv. Chim. Acta, 53 (1970) 1417—each incorporated herein by reference in its entirety].

In one embodiment, the thione-based ligands coordinating the central core platinum(II) atom are prepared by reacting carbon disulfide ($CS_2$) with diamines in diethyl ether solvent and refluxing the reaction mixture at 100-110° C. for 2-3 h. The clear yellow product was recrystallized from methanol.

In one embodiment, to prepare a dichloride platinum(II) complex, an $K_2PtCl_4$ aqueous solution and an aqueous solution of the prepared thione-based ligands are mixed and refluxed. The obtained product is filtered whilst hot and, the solvent is evaporated from the product.

In another embodiment, to prepare a dinitrate platinum(II) complex $AgNO_3$ is added to an aqueous solution of cisplatin and the mixture is stirred for 12-30 h in the dark at room temperature, then filtered. The prepared thione-based ligands are dissolved in a minimal amount of methanol which is then added to the filtrate and the mixture is stirred for 2-6 h. The obtained product is filtered and the solvent is evaporated from the product.

Method of Inhibiting Proliferation of Cancer Cells and Inducing Cancer Cell Death The present disclosure further provides a method of inhibiting proliferation of human cancer cells and inducing apoptosis of the human cancer cells in vitro or in vivo. Human cancer cells are contacted with 1-100 µM of a gold(III) complex in accordance with the present disclosure or a composition comprising the gold(III) complex at the defined concentration range, preferably 2-80 µM, more preferably 5-75 µM, even more preferably 10-60 µM, 12.5-60 µM, 15-60 µM, 20-60 µM, most preferably 20-55 µM, 25-55 µM 30-55 µM, 35-55 µM, 30-40 µM, 25-40 µM, 35-45 µM, 40-50 µM, 45-50 µM. The viability of cells can be determined by standard cell viability assays such as but not limited to ATP test, Calcein AM assay, clonogenic assay, ethidium homodimer assay, Evans blue assay, Fluorescein diacetate hydrolysis/propidium iodide staining assay, flow cytometry assay, formazan-based assays (MTT.XTT), green fluorescent protein assay, lactate dehydrogenase assay, methyl vilet assay, propidium iodide assay, Resazurin assay. Trypan Blue assay and TUNEL assay.

When contacted with one or more of the platinum(II) complexes at the defined concentration, the viability of the human cancer cells is reduced to at least 95%, preferably at least 85%, more preferably at least 75%, even more preferably at least 50%, at least 45%, at least 40%, at least 35%, at least 30%, at least 25%, at least 20%, most preferably at least 15%, at least 12.5%, at least 10%, at least 7.5%, at least 5%, at least 2.5%, at least 2%, at least 1% and at least 0.5%.

The half maximal inhibitory concentration ($IC_{50}$) is a measure of the effectiveness of a substance in inhibiting a specific biological or biochemical function. The $IC_{50}$ values of the gold(III) complexes against the human cancer cells are no higher than 175 µM, preferably at least no higher than 150 µM, more preferably no higher than 125 µM, no higher than 100 µM, even more preferably no higher than 80 µM, no higher than 75 µM, most preferably no higher than 60 µM, no higher than 50 µM and no higher than 45 µM. In some embodiments, the $IC_{50}$ value of the platinum complexes against human lung, breast or colon cancer cells, such as but not limited A549, MCF7 and HCT15 cell lines, are ranged 5-70 µM, preferably 7.5-65 µM, more preferably 10-60 µM, even more preferably 10-50 µM, most preferably 10-45 µM. In some embodiments, compared to cisplatin and carboplatin, the $IC_{50}$ values of the platinum(II) complexes provided herein are up to 50% lower, preferably 5-50% lower, more preferably 10-50% lower, even more preferably 25-50% times lower.

In some embodiments, the human cancer cells are derived from commercial cell line models, including but are not limited to HeLa cervical cancer cells, A549 lung cancer cells, HCT-15 colon cancer cells, HCT-8 or HRT-8 colon cancer cells, DLD-1 colon cancer cells, MCF-7 breast cancer cells, A2780 ovarian cancer cells. A2780-cis cisplatin-resistant ovarian cancer cells, PC3 prostatic cancer cells. DU-145 prostatic cancer cells, SGC7901 gastrointestinal cancer cells and SGC7901-cis cisplatin-resistant gastrointestinal cancer cells.

In other embodiments, the human cancer cells are cancer cells of a human patient who has been diagnosed with, is suspected of having, or is susceptible to or at risk of having at least one form of cancer, preferably prostate cancer and/or gastrointestinal cancer.

Methods of Treating Cancers and Combination Therapies

Cancers such as but not limited to sarcomas, carcinomas, melanomas, myelomas, gliomas and lymphomas can be treated or prevented with the platinum(II) complexes provided herein. In some embodiments, methods incorporating the use of at least one of the platinum(II) complexes of the present disclosure are effective in the treatment or prevention of cancer of the blood, brain, bladder, lung, cervix, ovary, colon, rectum, pancreas, skin, prostate gland, stomach, breast, liver, spleen, kidney, head, neck, testicle, bone (including bone marrow), thyroid gland or central nervous system. In some embodiments, these methods are especially effective in the treatment or prevention of cervical, colon and lung cancers.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment with one or more platinum(II) complexes or a pharmaceutical composition thereof, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99% or 100%, relative to the tumor size before treatment. In other embodiments, after treatment with the one or more platinum(II) complexes of a pharmaceutical composition thereof, the size of a tumor does not reduce but is maintained the same as the tumor size before treatment. Methods of assessing tumor size include but are not limited to CT Scan, MRI, DCE-MRI and PET Scan.

In some embodiments, the method for treating cancer and other proliferative disorders involves the administration of a unit dosage or a therapeutically effective amount of one or more of platinum(II) complexes or a pharmaceutical composition thereof to a mammalian subject (preferably a human subject) in need thereof. As used herein, "a subject in need thereof" refers to a mammalian subject, preferably a human subject, who has been diagnosed with, is suspected of having, is susceptible to, is genetically predisposed to or is at risk of having at least one form of cancer. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. The one or more of platinum(II) complexes or a pharmaceutical composition thereof may be administered in a single dose or multiple individual divided doses. In some embodiments, the interval of time between the administration of platinum(II) complexes or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, mixed diamine ligand platinum(II) complexes and one or more additional therapies are administered less than 1 day, 1 week, 2 weeks, 3 weeks, 4 weeks, one month, 2 months, 3 months, 6 months, 1 year, 2 years, or 5 years apart.

A physician or veterinarian having ordinary skill in the art can readily determine and prescribe the therapeutically effective amount of the pharmaceutical composition required. For example, the physician or veterinarian could start doses of the platinum(II) complexes of the invention employed in the pharmaceutical composition at levels lower than that required in order to achieve the desired therapeutic effect and gradually increase the dosage until the desired effect is achieved.

In general, a suitable daily dose of a platinum(II) complex of the present disclosure will be that amount of the compound which is the lowest dose effective to produce a therapeutic effect. Such an effective dose will generally depend upon the factors described above. Generally, oral, intravenous, intracerebroventricular and subcutaneous doses of the platinum(II) complex of this invention for a patient will range from 0.01-100 mg per kilogram of body weight per day (24 h), preferably 0.05-75 mg/kg/day, more preferably 0.1-50 mg/kg/day, even more preferably 0.5-50 mg/kg/day, 1.0-50 mg/kg/day, 5.0-50 mg/kg/day, 10-50 mg/kg/day, 20-50 mg/kg/day, 25-50 mg/kg/day.

If desired, the effective daily dose of the active compound, which is the platinum(II) complex in the present case, may be administered as two, three, four, five, six or more sub-doses administered separately at appropriate intervals throughout the day, optionally, in unit dosage forms. In certain aspects of the invention, dosing is one administration per day.

While it is possible for a platinum(II) complex of the present disclosure to be administered alone, it is preferable to administer the platinum(II) complex as a pharmaceutical formulation (composition).

In certain embodiments, a platinum(H) complex of the present disclosure or a pharmaceutical composition thereof may be used in combination with one or more other active pharmaceutical agents, preferably antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cisplatin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like. In one embodiment, a pharmaceutical composition may be formulated as such to incorporate at least one platinum(II) complex of the present disclosure and one or more other active pharmaceutical agents which may or may not be selected from the list above.

The following examples have been included to further describe protocols for synthesizing and characterizing certain platinum(II) complexes having thione-based heterocyclic ligands, and results thereof. It should be noted that these examples have been included for illustrative purposes, and are not intended to limit the scope of the appended claims.

In these examples, a series of complexes having a general formula of $[Pt(thione)_4]X_2$, ($X = Cl^-$, $NO_3^-$) was synthesized and fully characterized using analytical techniques and spectroscopic methods. NMR as well as X-ray crystallography data confirmed that the Pt(II) ion is bonded to the thione ligands through their sulfur atoms. Hydrogen bonding interactions in Complex (7) induce a bent see-saw distortion relatively the ideal square planar geometry. In vitro cytotoxicity studies showed that the compound $[Pt(EtImt)_4]Cl_2$ (2) is the most cytotoxically effective among the synthesized complexes and is two-fold better as a cytotoxic agent than cisplatin against MCF7 (human breast cancer) cell.

Example 1

Chemicals and Reagents

Potassium tetrachloridoplatinate(II), $K_2PtCl_4$ was purchased from Strem Chemicals, Inc. Carbon disulfide ($CS_2$) and diamines i.e. N-methyl-1,2-diaminoethane. N-ethyl-1,2-diaminoethane, N-propyl-1,2-diaminoethane and N-isopropyl-1,2-diaminoethane, N-ethyl-1,3-diaminopropane, 1,4-Diaminobutane, were obtained from Sigma Aldrich. Dulbecco's Modified Eagle Medium (DMEM). (3-(4,5-dimethylthiazol-2-yl)-2,5-diphenyltetrazolium Bromide) (MTT), Dimethyl sulfoxide (DMSO) and deuterated solvents were also obtained from Sigma Aldrich Chemical Co. All other solvents were obtained from Fluka Chemical Co. and used without further purification.

Example 2

Synthesis of Thione Ligands

The thione ligands were synthesized following a literature procedure by the reaction of carbon disulfide ($CS_2$) with diamines in diethyl ether solvent. The mixture was then refluxed at 100-110° C. for 2-3 h [G. D. Thorn, Can. J. Chem., 33 (1955) 1278; L. Maier, Helv. Chim. Acta, 53 (1970) 1417—each incorporated herein by reference in its entirety]. The clear yellow product was recrystallized from methanol.

Example 3

Synthesis of [Pt(thione)$_4$]Cl$_2$ Complexes (1)-(6)

K$_2$PtCl$_4$ (0.500 mmol) in 3.0 mL of water and thione ligand (2.00 mmol) in 25.0 mL hot water were mixed and refluxed for 4 h. A yellow solution was finally obtained. It was filtered whilst hot. The solvent was evaporated. Quality yellow-orange crystals of complex (1), suitable for X-ray diffraction was obtained by the slow evaporation of the solvent. The CHNS data, melting/decomposition points and % yield of the synthesized complexes are presented as below:

Complex (1) [Pt(MeImt)$_4$]Cl$_2$.2H$_2$O: C, 24.91 (25.06), H, 4.61 (4.73), N, 14.51 (14.62), S, 16.36 (16.73) decomposition point 262° C. and yield 58.9%, Complex (2) [Pt(EtImt)$_4$]Cl$_2$: C, 30.56 (30.53), H, 5.01 (5.12), N, 14.46 (14.24), S, 16.47 (16.30); decomposition point 225° C. and yield 64.3%: Complex (3) [Pt(PrImt)$_4$]Cl$_2$: C, 33.98 (34.20), H, 5.40 (5.47), N, 13.35 (13.30), S, 12.34 (12.22); decomposition point 106° C. and yield 89.3%; Complex (4) [Pt(i-PrImt)$_4$]Cl$_2$: C, 34.22 (34.20), H, 5.33 (5.47), N, 13.21 (13.30), S, 12.27 (12.22): melting point 145° C. and yield 92.5%; Complex (5) [Pt(EtDiaz)$_4$]Cl$_2$: C, 33.80 (34.19), H, 5.82 (5.74), N, 13.10 (13.29), S, 12.24 (12.22): melting point 113° C. and yield 52.5%; Complex (6) [Pt(Diap)$_4$]Cl$_2$: C, 30.27 (30.53), H, 5.22 (5.12), N, 14.13 (14.24). S, 16.12 (16.30); decomposition 285° C. and yield 35.3%.

Example 4

Synthesis of [Pt(iPrImt)$_4$](NO$_3$)$_2$.0.6(H$_2$O), Complex (7)

168.8 mg (1.000 mmol) of AgNO$_3$ was added to solution contain 150.06 mg (0.500 mmol) of cisplatin in 10.0 mL water and stirred for 24 h in the dark at room temperature, then filtered, 288.2 mg (2.000 mmol) of N-iPropyl-Imt dissolved in 10.0 mL Methanol was added to the filtrate. The brown solution was filtered after stirring for 3 h and the filtrate was kept at room temperature for evaporation to afford X-ray quality crystals. Complex (7) [Pt(iPrImt)$_4$](NO$_3$)$_2$.0.6(H$_2$O): C, 31.04 (31.78), H, 5.18 (5.48), N, 15.57 (15.44), S, 13.99 (14.14); melting point 119° C. and yield 42.9%.

Example 5

Stability and Solubility of Complexes (1)-(7)

Complexes (1), (5) and (6) were dissolved in DMSO-d$_6$ and their $^1$H NMR spectra were measured. The extent of decomposition over time was determined by comparing the NMR spectra collected after 1, 6, 12, 24, 48 and 72 h. No significant change in the chemical shifts and the splitting patterns of compounds (1 and 2) was observed in their time dependent $^1$H NMR spectra. Complex (1) was moderately soluble in CDCl$_3$ but completely soluble in DMSO and DMF. Complexes (2-7) were completely soluble in polar organic solvents i.e. CDCl$_3$, DMSO and DMF.

Example 6

Spectroscopic and Other Characterization Methods

The solid-state FTIR spectra of thione ligands and their corresponding Tetrakis(thione) platinum(II) chloride or nitrate complexes (1)-(7) were recorded on Nicolet 6700 FTIR Spectrometer using KBr pellets over the range 4000-400 cm$^{-1}$. $^1$H NMR spectra were obtained on Jeol JNM-LA 500 NMR spectrometer operating at a frequency of 500.00 MHz. $^{13}$C NMR spectra were obtained at the frequency of 125.65 MHz with $^1$H broadband decoupling at 298 K. The spectral conditions were: 32 k data points, 0.967 s acquisition time, 1.00 or 30.00 s pulse delay and 45° pulse angle. Elemental analyses for the synthesized platinum (II) thione complexes were performed on Perkin Elmer 2400 Series II CHNS/O Analyzer.

Example 7

X-Ray Diffraction Analysis

For Pt(II) complex (1), the X-ray diffraction data were recorded on a Bruker-Axs Smart Apex system equipped with a graphite monochromatized MoKα radiation (λ=0.71073 Å). The data were collected using SMART (SMART APEX software (5.05) for SMART APEX Detector, Bruker Axs Inc., Madison. Wis., USA). The data integration was performed using SAINT (SAINT Software (5.0) for SMART APEX Detector, Bruker Axs Inc. Madison. Wis., USA). An empirical absorption correction was carried out using SADABS (G. M. Sheldrick, SADABS. Program for Empirical Absorption correction of Area detector Data. University of Gottingen, Germany, 1996). The structure was solved with the direct methods and refined by a full matrix least square methods based on F$^2$, using the structure determination package SHELXTL (G. M. Sheldrick, SHELXTL V5.1 Software. Bruker Axs Inc., Madison. Wis., USA, 1997) based on SHELX 97 [G. M. Sheldrick, Acta Crystallogr., A64 (2008) 112-122—incorporated herein by reference in its entirety]. Graphics were generated using ORTEP-3 and Mercury [L. Farrugia, J. Appl. Crystallogr., 30 (1997) 565; C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Crystallogr., 41(2008) 466—each incorporated herein by reference in its entirety]. By using the riding model, H-atoms other than those of the water molecules were included at calculated positions. Nitrogen atoms belonging to the NH groups were assumed to have sp$^2$ hybridization. The hydrogen atoms of the water molecules could not be located. For Pt(II) complex (7), the intensity data were collected at 173K (−100° C.) on a Stoe Mark II-Image Plate Diffraction System (Stoe & Cie. (2009). X-Area & X-RED32. Stoe & Cie GmbH, Darmstadt, Germany). equipped with a two-circle goniometer and using MoKα graphite monochromated radiation (λ=0.71073 Å). The structure was solved by direct methods with SHELXS-2014 [G. M. Sheldrick, Acta Crystallogr., A64 (2008) 112-122—incorporated herein by reference in its entirety]. The refinement and all further calculations were carried out with SHELXL-2014 [G. M. Sheldrick. Acta Crystallogr., A64 (2008) 112-122—incorporated herein by reference in its entirety]. The H-atoms were either located from Fourier difference maps and freely refined or included in calculated positions and treated as riding atoms using SHELXL default parameters. The non-H atoms were refined anisotropically, using weighted full-matrix least-squares on $F^2$. Empirical or multiscan absorption corrections were applied using the MULSCANABS routines in PLATON [A. L. Spek, Acta Cryst. D65 (2009) 148—incorporated herein by reference in its entirety]. A summary of crystal data and refinement details for platinum(II) complexes (1) and (7) are given in Table 1.

TABLE 1

Crystal and structure refinement data for Complexes (1) and (7)

| Parameter | Complex (1) | Complex (7) |
|---|---|---|
| CCDC deposit no. | 902467 | 1008031 |
| Empirical formula | $C_{16}H_{36}Cl_2N_8O_2PtS_4$ | $C_{24}H_{49.20}N_{10}O_{6.60}PtS_4$ |
| Formula weight | 766.76 | 906.86 |
| Temperature (K) | 296 (2) | 173 (2) |
| Wavelength (Å) | 0.71073 | 0.71073 |
| Crystal system | Triclinic | Tetragonal |
| Space group | P-1 | $P4_32_12$ |
| Unit cell dimensions | | |
| a (Å) | 9.011 (2) | 11.608 (3) |
| b (Å) | 9.424 (2) | 11.608 (3) |
| c (Å) | 9.627 (2) | 27.182 (1) |
| α (°) | 92.275 (4) | 90 |
| β (°) | 99.333 (4) | 90 |
| γ (°) | 116.185 (3) | 90 |
| Volume (Å$^3$) | 718.2 (3) | 3662.7 (2) |
| Z | 1 | 4 |
| Calc. density (g · cm$^{-3}$) | 1.773 | 1.645 |
| Absorp. coefficient (mm$^{-1}$) | 5.39 | 4.11 |
| F(000) | 380 | 1832 |
| Crystal size (mm) | 0.27 × 0.22 × 0.15 | 0.45 × 0.35 × 0.20 |
| θ range (°) | 2.16-28.37 | 1.9-26.1 |
| Limiting indices | $-12 \le h \le 11$ | $-14 \le h \le 14$ |
| | $-12 \le k \le 12$ | $-14 \le k \le 13$ |
| | $-12 \le l \le 12$ | $-32 \le l \le 33$ |
| Max and min transmission | $T_{min} = 0.3239, T_{max} = 0.4986$ | $T_{min} = 0.7681, T_{max} = 1.0000$ |
| Data/restraints/parameters | 3552/0/153 | 3457/5/230 |
| Goodness-of-fit on F$^2$ | 1.041 | 0.875 |
| Final R indices [I > 2σ (I)] | $R_1 = 0.0255, wR_2 = 0.0543$ | $R_1 = 0.0153, wR_2 = 0.0265$ |
| R indices (all data) | $R_1 = 0.0193, wR_2 = 0.0545$ | $R_1 = 0.0259, wR_2 = 0.0269$ |
| Largest diff. Peak and hole (e Å$^{-3}$) | 1.310 and −0.842 | 0.34 and −0.75 |

Example 8

MTT Assay for In Vitro Cytotoxic Studies of [Pt(Thione)$_4$]Cl$_2$ Compounds Against Human Cancer Cell Lines In the present disclosure, [Pt(thione)$_4$]Cl$_2$ complexes (1)-(7) were tested for their in vitro cytotoxic effects against MCF7 (human breast cancer), HCT15 (human colon adenocarcinoma), HeLa (human cervical cancer) and A549 (human lung carcinoma) cell lines as reported [M. Altaf, M. Monim-ul-Mehboob, A. A. Isab, V. Dhuna, G. Bhatia, K. Dhuna and S. Altuwaijri, New J. Chem., 39 (2015) 377—incorporated herein by reference in its entirety]. The cells were seeded at 3×10$^3$ cells/well in 100 µL DMEM containing 10% Fetal Bovine Serum (FBS) in 96-well tissue culture plate and incubated for 72 h at 37° C., 5% CO, in air and 90% relative humidity in CO$_2$ incubator. After incubation, 100 µL of 50, 25, 12.5 and 6.25 µM solutions of platinum(II) complexes, prepared in Dulbecco's Modified Eagle's Medium (DMEM), were added to the cells and the cultures were incubated for 24 h. The medium of wells was discarded and 100 µL DMEM containing MTT (0.5 mg/ml) was added to the wells and incubated in CO$_2$ incubator at 37° C. in dark for 4 h. After incubation, a purple colored formazan produced in the cells appeared as dark crystals in the bottom of the wells. The culture medium was discarded from each well carefully to prevent disruption of monolayer and 100 µL of dimethyl sulfoxide (DMSO) was added in each well. The solution in the wells was thoroughly mixed to dissolve the formazan crystals which produce a purple solution. The absorbance of the 96 well-plates was taken at 570 nm with Labsystems Multiskan EX ELISA reader against a reagent blank. The experimental results are presented as micro-mole concentration of 50% cell growth inhibition (IC$_{50}$) of each drug. The MTT assay was performed in three independent experiments, each in triplicate.

Example 9

FTIR Spectroscopic Characterization

The most important selected FTIR frequencies are quoted in Table 2. As reported in the literature, the assignment of the thioamides absorptions of the free thiones and their related compounds is not straightforward. This is due to the strong coupling between thiocarbonyl absorption with various bond absorptions in the fingerprint region of the FTIR spectrum [J. Jolley, W. I. Cross, R. G. Pritchard, C. A. McAuliffe, and K. B. Nolan, Inorg. Chim. Acta, 315 (2001) 36; J. Lin, G. Lu, L. M. Daniels, X. Wei, J. B. Sapp, and Y. Deng, J. Coord. Chem., 61 (2008) 2457; M. Altaf, H. Stoeckli-Evans, A. Cuin, D. N. Sato, F. R. Pavan, C. Q. F. Leite, S. Ahmad, M. Bouakka, M. Mimouni, F. Z. Khardli, and T. B. Hadda, Polyhedron, 62 (2013) 138; P. Castan and J. Laurent, Transition Met. Chem., 5 (1980) 154—each incorporated herein by reference in its entirety].

Nevertheless, a strong and broad band in the range of 1400-1600 cm$^{-1}$ appears for all the thione ligands and their related complexes. Based on the data of the previous literature, this band must be due to (N—H) deformation and (N—C—N) antisymmetric stretching. This band is often split and significantly shifted to higher frequency upon complexation; this is an indication of the increase in the double bond character of the C—N bond due to the coordination through sulfur [M. Altaf, H. Stoeckli-Evans, A. Cuin, D. N. Sato, F. R. Pavan, C. Q. F. Leite, S. Ahmad, M. Bouakka, M. Mimouni, F. Z. Khardli, and T. B. Hadda, Polyhedron, 62 (2013) 138; P. Castan and J. Laurent, Transition Met. Chem., 5 (1980) 154; B. H. Abdullah, M. A. Abdullah, and S. A. Al-Jibori, Asian J. Chem., 19 (2007) 1334—each incorporated herein by reference in its entirety. The band observed in the range of the 3220-3300 cm$^{-1}$ regions for most of the thione ligands and their related complexes is directly assigned for N—H stretching vibrations [J. Jolley, W. I. Cross, R. G. Pritchard, C. A. McAuliffe, and K. B. Nolan, Inorg. Chim. Acta, 315 (2001) 36; J. Lin, G. Lu, L. M. Daniels, X. Wei, J. B. Sapp, and Y. Deng, J. Coord. Chem., 61 (2008) 2457; M. Altaf, H. Stoeckli-Evans, A. Cuin, D. N. Sato, F. R. Pavan, C. Q. F. Leite, S. Ahmad, M. Bouakka, M. Mimouni, F. Z. Khardli, and T. B. Hadda, Polyhedron, 62 (2013) 138; P. Castan and J. Laurent, Transition Met. Chem., 5 (1980) 154; A.-M. Esmadi, Asian J. Chem., 13 (2001) 128—each incorporated herein by reference in its entirety]. This band is shifted to higher frequencies for most of the platinum(II) complexes due to the increase in double bond character which also supports the idea of coordination through sulfur of thiocarbonyl in the thione form. The assignment of thiocarbonyl frequencies is the most difficult part in the FTIR spectra because it strongly couples with other bonds within the molecule and gives rise to many bands in the fingerprint region. Many absorption bands in the FTIR spectrum of the free thiones, for instance MeImt: 1236, 1111, 957, 670, 637, 612, and 516 cm$^{-1}$, have shifted to lower wave number with no more than 21 cm$^{-1}$ in its related corresponding complex, and could be assigned to thiocarbonyl frequencies [J. Lin, G. Lu, L. M. Daniels, X. Wei, J. B. Sapp, and Y. Deng, J. Coord. Chem., 61 (2008) 2457—incorporated herein by reference in its entirety]. The same pattern of this shift has been noticed for most of the platinum(II) complexes which indicate the presence of the Pt—S bond. Finally, it seems appropriate to obtain more definitive evidence of the coordination site through another diagnostic tool, such as, NMR spectroscopy as well as X-ray crystallography, which will be discussed in the forthcoming parts.

TABLE 2

Selected mid-FTIR frequencies, ν(cm$^{-1}$) for Tetrakis(thione)Pt(II) complexes (1)-(7).

| Compound | $v_{(N-H)}$, cm$^{-1}$ | $v_{(C=S)}$, cm$^{-1}$ |
|---|---|---|
| MeImt | 3200 m | 515 s |
| (1) | 3172 m | 503 s |
| EtImt | 3188.2 | 514 |
| (2) | 3426 s | 497 |
| PrImt | 3205 m | 514 s |
| (3) | 3202 s | 507 sh |
| i-PrImt | 3208.2 | 494, 526 |
| (4) | 3202 s | 507 sh |
| EtDiaz | 3220 m | 453 s, 509 sh |
| (5) | 3249 b | 443 m, 512 sh |
| Diap | 3214 s | 526 |
| (6) | 3186 b | 514 sh |
| (7) | 3209 s | 489, 520 sh |

Abbreviations:
m = medium,
b = broad,
s = strong,
sh = shoulder

Example 10

Solution and Solid-State NMR Characterization

The $^1$H NMR chemical shifts of the free thione ligands and their corresponding complexes were studied in 50:50% v/v ratio of a mixture of CDCl$_3$ and DMSO solvents, whereas complex (5) was studied in CDCl$_3$. The $^1$H NMR solution-state data are given in Table 3.

The N—H protons of the coordinated thiones are shifted toward high frequency with respect to the free thiones. This large de-shielding of the N—H protons is an indication of the relatively more double bond character of the C—N bond upon coordination to Pt(II) which is consistent with the coordination of thiourea or its derivatives to the metal [P. Castan and J. Laurent, Transition Met. Chem., 5 (1980) 154; S. Schrider and W. Preetz, Zeitschrift für anorganische und allgemeine Chemie 626 (2000) 1757; A. A. Isab and M. I. M. Wazeer, J. Coord. Chem., 58 (2005) 529: A. A. Isab, S. Ahmad, and M. Arab, Polyhedron, 21 (2002) 1267—each incorporated herein by reference in its entirety]. The appearance of a N—H signal is a sign of coordinating to Pt(II) via the thione group.

The H-4 protons of coordinated thiones are slightly downfield shifted in comparison to the free thiones due to double bond character of the C—N bond upon coordination to Pt(II) center through sulfur of thiocarbonyl in thione ligands. There is no general trend, observed in chemical shifts of H-5 and H-6 coordinated protons owing to the different alkyl (methyl, ethyl, n-propyl and iso-propyl) groups attached to nitrogen atom of Imt containing ligands and different ring strain in R-Imt, EtDiaz and Diap ligands respectively.

The $^{13}$C NMR solution-state data are given in Table 4. On the other hand, $^{13}$C NMR signal for the thiocarbonyl carbon in the all complexes shifted upfield by 8.0 to 11.0 ppm with respect to the free ligands. This shift in thiocarbonyl carbon and NH proton signals is attributed to the decrease in C=S bond order and increase in C—N bond order upon complexation [P. Castan and J. Laurent, Transition Met. Chem., 5 (1980) 154; A. A. Isab and M. I. M. Wazeer, J. Coord. Chem., 58 (2005) 529—each incorporated herein by reference in its entirety]. The solid state $^{13}$C NMR, data shown in Table 4, indicates that the complexation of Pt(II) center with the thiones resulted in shielding of thiocarbonyl carbons in the synthesized complexes by about 8 to 10 ppm in comparison with their free thione ligands [M. I. M. Wazeer, A. A. Isab, and A. El-Rayyes, Spectroscopy 18 (2004) 113—incorporated herein by reference in its entirety]. This also confirms that the ring form of thione is retained in the complexes. The diap ligand and the corresponding complex (6) showed 3 peaks in the thiocarbonyl region. This may be attributed to the different conformations of the 7-membered ring. According to the solid-state $^{15}$N spectra (Table 5), the nitrogens in the synthesized complexes are about 5 to 8 ppm de-shielded in comparison with their free ligands, which confirm the increase in C—N bond order upon complexation.

TABLE 3

$^1$H chemical shifts (ppm) of the thiones and their Tetrakis(thione)Pt(II) complexes (1)-(7) in CDCl$_3$.

| Species | N—H | H-4 | H-5 | H-6 | N—C1—H | N—C2—H |
|---|---|---|---|---|---|---|
| MeImta | 8.02 | 3.72 | 3.58 | | 3.14 | |
| (1)$^a$ | 9.41 | 3.78 | 3.58 | | 3 | |
| EtImt$^b$ | 5.67 | 3.7 | 3.58 | | 3.67 | 1.2 |
| (2) | 9.67 | 3.71 | 3.56 | | 3.67 | 1.19 |
| PrImt$^b$ | 5.88 | 3.71 | 3.58 | | 3.56 | 1.64, 0.96$^d$ |
| (3) | 9.58 | 3.73 | 3.58 | | 3.46 | 1.63, 0.95$^d$ |
| i-PrImt$^b$ | 5.63 | 3.61 | 3.57 | | 4.82 | 1.19 |
| (4) | 9.65 | 3.82 | 3.73 | | 4.45 | 1.2 |
| EtDiaz$^b$ | 6.31 | 3.34 | 2.01 | 3.28 | 3.91 | 1.23 |
| (5) | 9.39 | 3.47 | 2 | 3.43 | 3.76 | 1.24 |
| Diap$^b$ | 6.69 | 3.26 | 1.75 | 1.75 | | |
| (6)$^c$ | 9.09 | 3.3 | 1.71 | 1.71 | | |
| (7)$^a$ | 8.77 | 3.68 | 3.57 | | 4.3 | 1.06 |

$^a$$^1$H resonances in DMSO.
$^b$$^1$H resonances of these thiones in DMSO are reported in literature [G. D. Thorn, Can. J. Chem., 33 (1955) 1278; L. Maier, Helv. Chim. Acta, 53 (1970) 1417; D. Kovala-Demertzi, M. A. Demertzis, J. R. Miller, C. Papadopoulou, C. Dodorou, G. Filousis, J. Inorg. Biochem. 86 (2001) 555 - each incorporated herein by reference in its entirety].
$^c$$^1$H resonances of these complexes in 50:50 (v/v) mixture of CDCl$_3$ and DMSO.
$^d$N—C3—H

TABLE 4

$^{13}$C chemical shifts (ppm) of the thiones and their Tetrakis(thione)Pt(II) complexes (1)-(7) in CDCl$_3$.

| Species | C-2 | C-4 | C-5 | C-6 | N—C1 | N—C2 |
|---|---|---|---|---|---|---|
| MeImt$^a$ | 182.9 | 40.6 | 50.18 | | 33.39 | |
| (1)$^a$ | 173.55 | 42.27 | 51.68 | | 33.6 | |

TABLE 4-continued $^{13}$C chemical shifts (ppm) of the thiones and their Tetrakis(thione)Pt(II) complexes (1)-(7) in CDCl$_3$.

| Species | C-2 | C-4 | C-5 | C-6 | N—C1 | N—C2 |
|---|---|---|---|---|---|---|
| EtImt[b] | 183.02 | 41.56 | 47.85 | | 41.23 | 12.02 |
| (2) | 174.41 | 42.78 | 49.11 | | 41.78 | 12.44 |
| PrImt[b] | 183.72 | 41.38 | 48.63 | | 48.63 | 20.44, 11.18[d] |
| (3) | 174.9 | 42.8 | 49.66 | | 48.48 | 20.60, 11.09[d] |
| i-PrImt[b] | 182.51 | 41.48 | 42.85 | | 46.9 | 19.32 |
| (4) | 173.89 | 42.73 | 44 | | 47.59 | 19.68 |
| EtDiaz[b] | 176.88 | 45.41 | 21 | 40.73 | 48.92 | 11.99 |
| (5) | 168.55 | 46.9 | 20.56 | 40.38 | 49.08 | 12.76 |
| Diap[b] | 189.42 | 46.28 | 27.33 | 27.33 | | |
| (6)[c] | 178.27 | 46.25 | 26.43 | 26.43 | | |
| (7) | 174.17 | 42.71 | 44.65 | | 48.78 | 19.2 |

[a]$^{13}$C resonances in DMSO.
[b]$^{13}$C resonances of these thiones in DMSO are reported in literature [15, 16, 42].
[c]$^{13}$C resonances of these complexes in 50:50 (v/v) mixture of CDCl$_3$ and DMSO.
[d]N—C3

TABLE 5

Solid-state $^{15}$N and $^{13}$C NMR chemical shifts (ppm) for free thione ligands and their Tetrakis(thione)Pt(II) complexes (1), (5) and (6).

| Species | N-1 | C-2 | C-4 | C-5 | C-6 | N—C1 | N—C2 |
|---|---|---|---|---|---|---|---|
| MeImt | −275.29 | −277.41[a] | 180.97 | 40.68 | 50.85 | | 34.19 |
| (1) | −269.03 | −279.95[a] | 173.03 | 43.32 | 52.50 | | 35.07 32.90[b] |
| EtDiaz | −271.38 | −274.85[a] | 175.76 | 41.62 | 21.58 | 46.68 | 46.68 12.77 |
| (5) | −258.24 | −270.75[a] | 168.82 166.60 | 41.58 | 20.69 | 48.4 | 48.4 12.73 |
| Diap | −265.55 | | 188.22 186.17 183.08 | 48.62 45.75 44.50 | 27.80 | 27.80 | |
| (6) | −259.12 | −263.62[a] | 181.70 180.16 174.79 | 48.47 45.81 43.35 | 28.38 23.97 | 28.38 23.97 | |

[a]Resonance due to non-equivalent amino (—NH$_2$) groups
[b]Resonance due to non-equivalent methyl (—CH$_3$) groups Example 11

Crystal Structure Determination of Complexes (1) and (7)

The X-ray structure of Complex (1) is shown in FIG. 1. Displacement ellipsoids are drawn at the 30% probability level. The hydration water molecule was omitted for clarity. (Pt1-S1, 2.3243(9) Å; Pt1-S2, 2.3263(9) Å; S1-Pt1-S2, 92.11(3)°; S1-Pt1-S2$^i$, 87.89(3)°). Symmetry codes: i=−x, −y, −z; ii=−1−x, −1−y, −z; iii=1+x, 1+y, z. As seen in FIG. 1, the platinum (II) ion is located on an inversion center and bound to the sulfur atoms of four N-methylimidazolidine-2-thione (MeImt) ligand molecules in a distorted square planar geometry. The Pt—S bond distances are 2.3243(9) Å and 2.3263(9) Å and the S—Pt—S bond angle is 92.11(3)°. These values are in agreement with those reported for the complexes tetrakis(Imidazolidine-2-thione)platinum(II) iodide and tetrakis(thiourea-S)platinum(II) chloride [J. Lin, G. Lu, L. Daniels, X. Wei, J. Sapp, and Y. Deng, J. Coord. Chem., 61 (2008) 2457; L. Fuks, N. Sadlej-Sosnowskab. K. Samochockac. W. Starostaa, Journal of Molecular Structure, 740 (2005) 22—each incorporated herein by reference in its entirety]. The SCN$_2$ moieties of the two ligand molecules are essentially planar with the following bond lengths (d(S1-C1)=1.705(4)Å, d(C1-N1)=1.321(5) A, d(C1-N2)=1.468(5) A) and (d(S2-C5)=1.709(3)Å, d(C5-N3)=1.313(5) A, d(C5-N4)=1.333(4) A). The N—H groups (N1-H1 and N3-H3) of two cis-thione ligands are engaged in hydrogen bonding with a common chloride ion giving rise to a hydrogen bonding bridge [N—H . . . Cl . . . H—N] as shown in FIG. 1.

Figure 2:
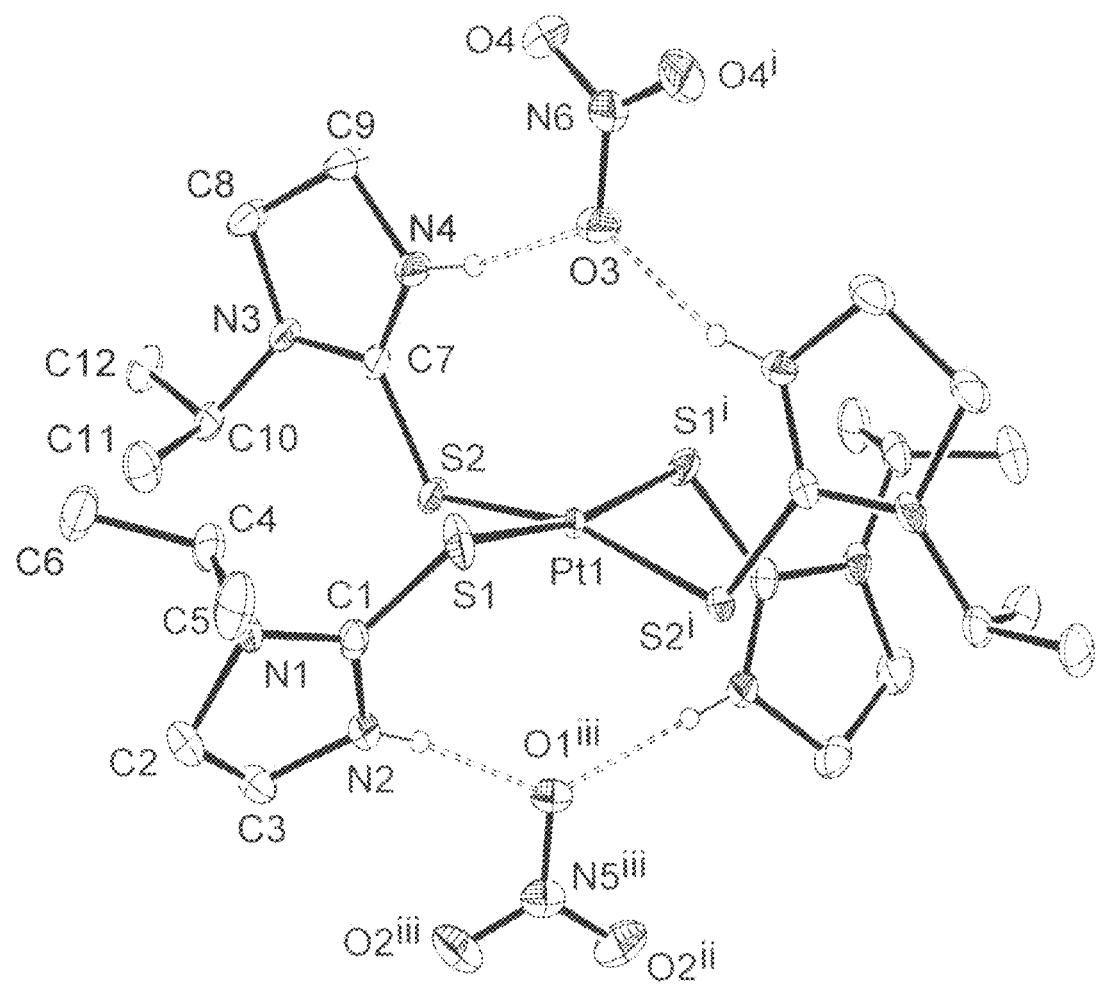
FIG. 2 is an ORTEP diagram of Complex (7), showing the molecular structure of complex (7) obtained by X-ray diffraction and the atomic labeling scheme.

The X-ray structure of Complex (7) is shown in FIG. 2. Displacement ellipsoids are drawn at the 30% probability level. The hydration water molecule and hydrogen atoms other N—H were omitted for clarity. (Pt1-S1, 2.3035(8) Å; Pt1-S2, 2.3222(8) Å; S1-Pt1-S2, 92.17(4)°; S1-Pt1-S2, 89.34(4)°). Symmetry codes: i=y, x, −z; ii=−y+½, x−½, z−¼; iii=x−½, −y+½, −z+¼. Similar to Complex (1), Pt(II) ion in Complex (7) is bonded to four sulfur atoms, each belonging to a N-isopropylimidazolidine-2-thione (iPrImt) ligand. The Pt—S bond lengths are in the range 2.3035(8)-2.3222(8) Å while the S—Pt—S bond angles are in the range 89.34(4)-92.17(4)°. The bond distances are similar to those found for Complex (1) and the related compound tetrakis(1-Methyl-4-imidazoline-2-thione)platinum(II) chloride dihydrate [P. J. M. W. L. Birker, J. Reedijk; G. C. Verschoor, J. Jordanov, Acta Crystallographica Section B-Structural Science, 38 (1982) 2245—incorporated herein by reference in its entirety]. Similar to Complex (1), the SCN$_2$ moieties of the four ligand molecules of Complex (7) are also essentially planar with the S—C and C—N bond lengths in the ranges (1.706(4)-1.709(4)) Å and (1.321(4)-1.350(4) Å) respectively. However, the geometry around the platinum ion exhibits interesting features. The structure presents a deviation from the ideal square planar geometry reminiscent of a bent seesaw distortion where the trans-sulfur atoms S1 and S1' are displaced above the [PtS$_4$] mean plane by 0.2603(9) Å whereas S2 and S2$^{ii}$ are displaced below the mean plane by 0.2723(8) Å. For Complex (7) the geometry of the Pt coordination geometry can be more precisely described by the $\tau_4$ (Tor4) parameter, as distorted square-planar with a $\tau_4$ value of 0.19 (the two largest angles in this four-coordinate species are 168.15(6) and 165.38(5)°) [L. Yang, D. R. Powell and R. P. Houser. Dalton Trans., (2007) 955-964—incorporated here by reference in its entirety]. In Complex (1), the Pt coordination geometry, which is located on an inversion center, has a perfect square-planar geometry with $\tau_4$=0 [the two largest angles in this four-coordinate species are both 180°]. A closer look to hydrogen bonding interactions reveals that the thione ligands of each of the two trans pairs are engaged in hydrogen bonding interactions with one oxygen atom of the nitrate counter ion, playing the role of a bridge between them: [N—H . . . O$_{NO2}$ . . . H—N]. This H-bonding scheme gives rise to two decametallacycles [PtSCNH . . . O . . . HNCS] in which the trans-sulfur atoms are pushed out of the [PtS$_4$] mean plane (FIG. 3) and hence resulting in the minor seesaw distortion.

Example 12

In Vitro Cytotoxicity of [Pt(Thione)$_4$]Cl$_2$ Compounds Against A549, MCF7, HCT15 and HeLa Human Cancer Cell Lines

The cytotoxicity of the synthesized complexes (1)-(7), cisplatin and carboplatin were evaluated in vitro against four human cancers: A549 (human lung carcinoma), MCF7 (human breast cancer), HCT15 (human colon adenocarcinoma), and HeLa (human cervical cancer) cell lines. The exposure of the cells to the increase in the concentrations of the complexes resulted in a dose dependent cytotoxic effect. This cytotoxic effect was obtained by the stipulated increase in the concentrations of the complexes and cisplatin against fixed number of human cancer cells. The IC$_{50}$ concentration of the complexes and Cisplatin for different human cell lines was obtained from curves between the complexes concentration and percentage viability of the cells. The effect of concentration of complexes (1)-(7) in μM on the percentage viability of A549, MCF7, HCT15 and HeLa cells have been shown graphically in FIGS. 3, 4, 5 and 6, respectively (Supplementary Material). The standard anticancer agents cisplatin and carboplatin were also included in these bar graphs for the purpose of comparison with complexes (1)-(7).

Figure 3:
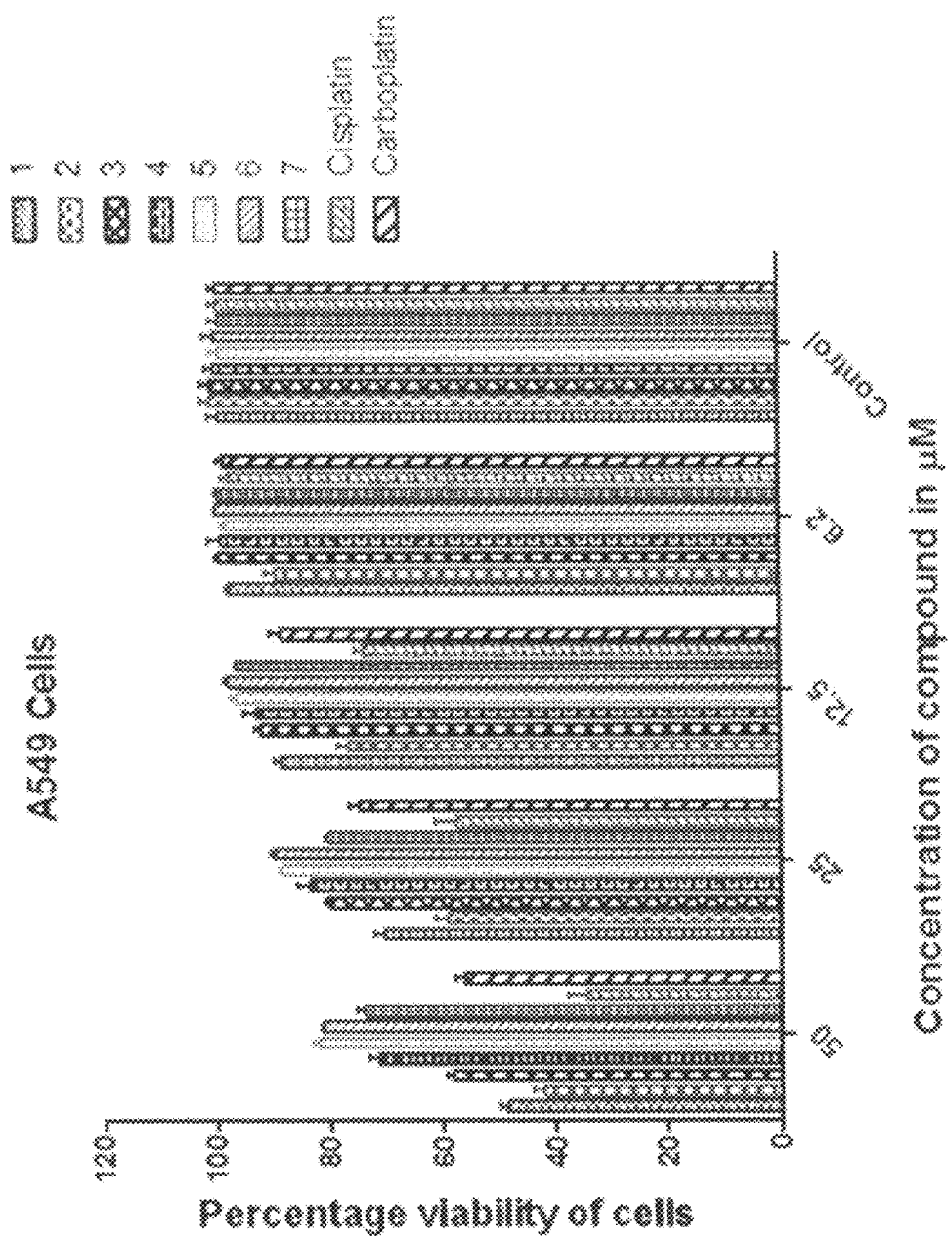
FIG. 3 is a bar graph showing the effects of concentration of Pt(II) complexes (1)-(7), cisplatin and carboplatin (in μM) on the percentage viability of A549 cancer cells.

Referring to Table 6 and FIG. 3, the IC$_{50}$ values of the complexes ranged far and wide between 36.93 μM and 137.16 μM for A549 cell line. Complex (2) has in vitro cytotoxicity comparable to that of cisplatin and almost two times better than that of carboplatin. Complexes (1) and (3) have in vitro cytotoxicity in between cisplatin and carboplatin. Complexes (4) and (7) have almost equal cytotoxicity. The IC$_{50}$ values of the complexes ranged throughout between 11.40 to 120.86 μM for MCF7 cell line as given in Table 6.

Figure 4:
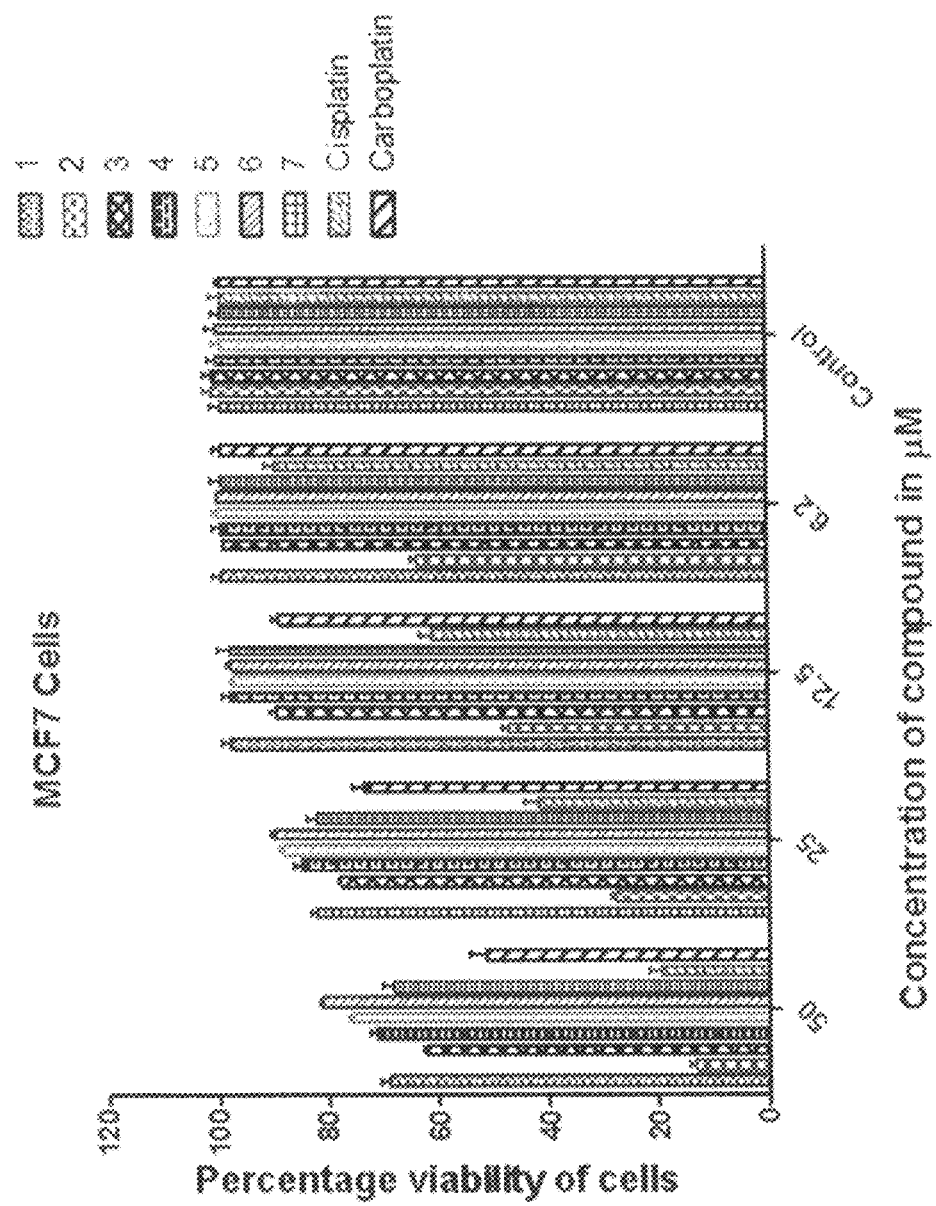
FIG. 4 is a bar graph showing the effects of concentration of Pt(II) complexes (1)-(7), cisplatin and carboplatin (in μM) on the percentage viability of MCF7 cancer cells.

Referring to Table 6 and FIG. 4, Complex (2) was found to be a two-fold better cytotoxic agent against the MCF7 cell line than cisplatin with IC$_{80}$ values 11.40 and 21.33 μM respectively. Complexes (1), (4) and (7) have very similar cytotoxic data and efficacy.

Figure 5:
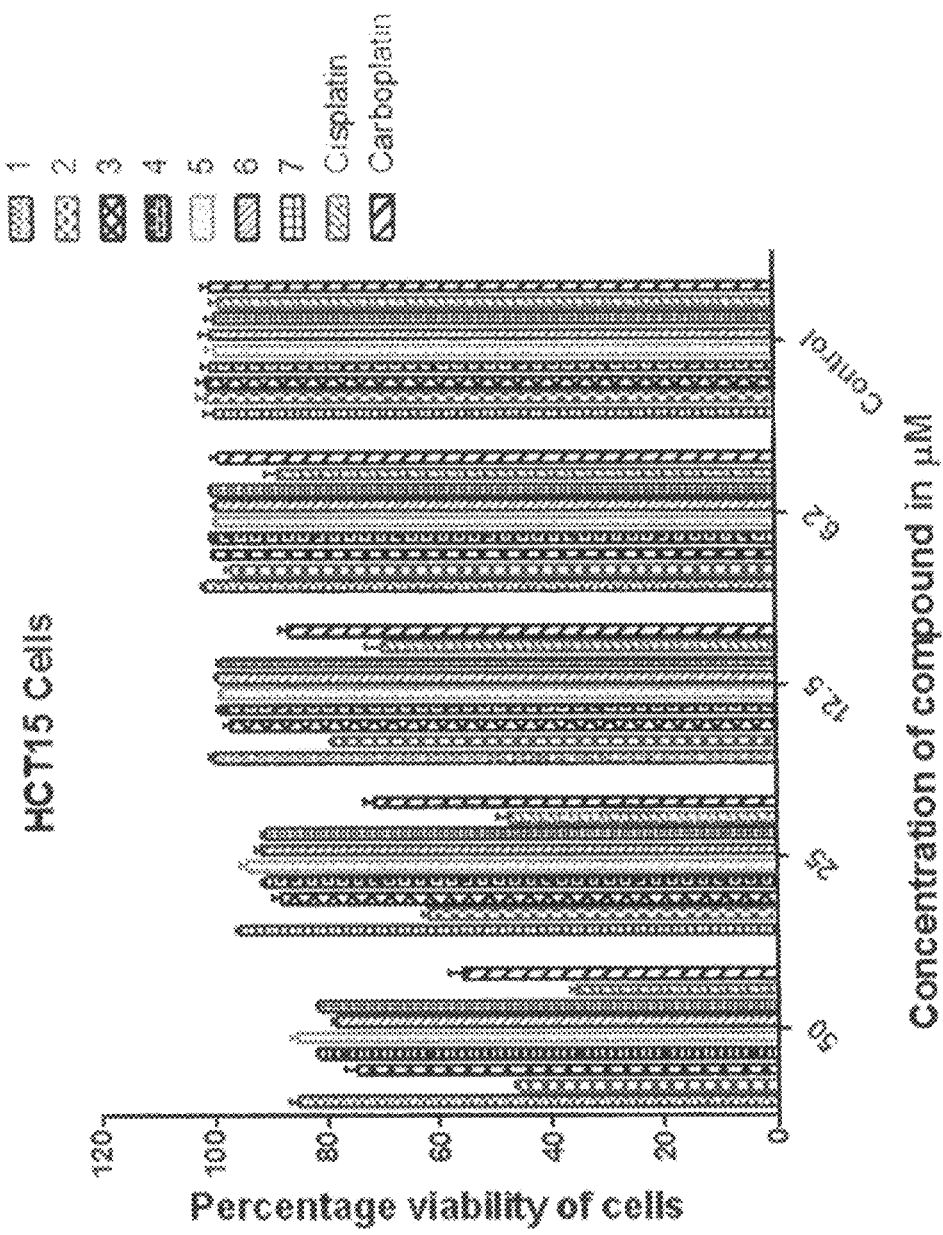
FIG. 5 is a bar graph showing the effects of concentration of Pt(II) complexes (1)-(7), cisplatin and carboplatin (in μM) on the percentage viability of HCT15 cancer cells.

Referring to Table 6 and FIG. 5, the IC$_{50}$ values of Complexes (1)-(7) against HCT15 cells ranged in between 26.63 μM and 158.88 μM for HCT15 cell line as given in Table 6. The in vitro cytotoxic efficacy of Complex (2) lies in between cisplatin's and carboplatin's. The IC$_{50}$ values of the complexes ranged at least and utmost between 18.07 μM and 166.41 μM for HeLa cell line as given in Table 6. Complexes (1)-(7) were not better than cisplatin and carboplatin.

Figure 6:
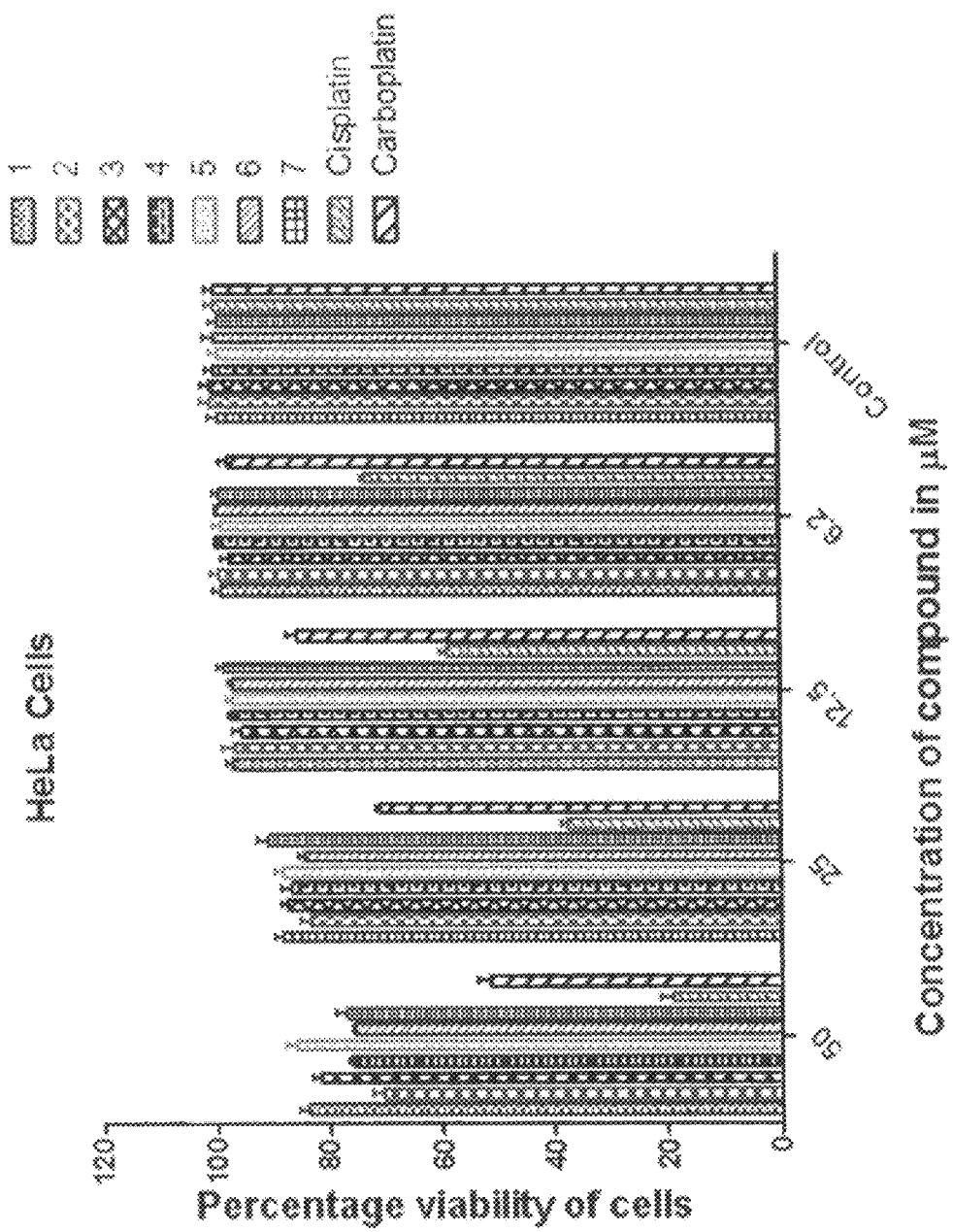
FIG. 6 is a bar graph showing the effects of concentration of Pt(II) complexes (1)-(7), cisplatin and carboplatin (in μM) on the percentage viability of HeLa cancer cells.

Referring to Table 6 and FIG. 6, the in vitro cytotoxicity of Complexes (1)-(7) against HeLa cell lines was found to be less than cisplatin. These results are consistent with a significant selective cytotoxicity of Complex (2) against particular cancer cell lines and its tendency to undergo ligand exchange with biomolecules like proteins and DNA [Seerat-ur-Rehman, A. A. Isab, M. N. Tahir, T. Khalid, M. Saleem, H. Sadaf, S. Ahmad, Polyhedron, 36 (2013) 68; S. Ahmad, A. A. Isab, S. Ali, A. R. Al-Arfaj, Polyhedron, 25 (2006) 1631—each incorporated herein by reference in its entirety].

TABLE 6

In vitro cytotoxic data of Tetrakis(thione)Pt(II) complexes (1)-(7), cisplatin and carboplatin against A549, MCF7, HCT15 and HeLa cancer cell lines.

| Compound | IC$_{50}$ ± SEM[a] | | | |
|---|---|---|---|---|
| | A549 | MCF7 | HCT15 | HeLa |
| 1 | 55.46 ± 1.08 | 74.59 ± 1.54 | 146.94 ± 1.77 | 141.63 ± 2.42 |
| 2 | 37.10 ± 1.23 | 11.40 ± 1.34 | 41.56 ± 1.53 | 79.19 ± 1.95 |
| 3 | 59.25 ± 2.60 | 62.85 ± 1.51 | 95.58 ± 2.14 | 132.61 ± 1.97 |
| 4 | 85.74 ± 1.35 | 78.07 ± 1.45 | 121.84 ± 1.75 | 95.44 ± 0.88 |
| 5 | 137.16 ± 1.77 | 95.04 ± 2.02 | 158.88 ± 2.90 | 166.41 ± 2.01 |
| 6 | 119.32 ± 2.25 | 120.86 ± 3.36 | 107.54 ± 2.03 | 92.50 ± 2.45 |
| 7 | 84.16 ± 1.09 | 74.35 ± 1.28 | 116.26 ± 2.09 | 99.90 ± 2.25 |
| Cisplatin | 36.93 ± 1.88 | 21.33 ± 1.54 | 26.63 ± 1.07 | 18.07 ± 1.36 |
| Carboplatin | 70.23 ± 1.70 | 53.23 ± 1.65 | 63.30 ± 1.58 | 55.03 ± 0.94 |

[a]Limit of errors are given in SEM as standard deviations determined from at least three independent experiments.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A platinum(II) complex of Formula I:

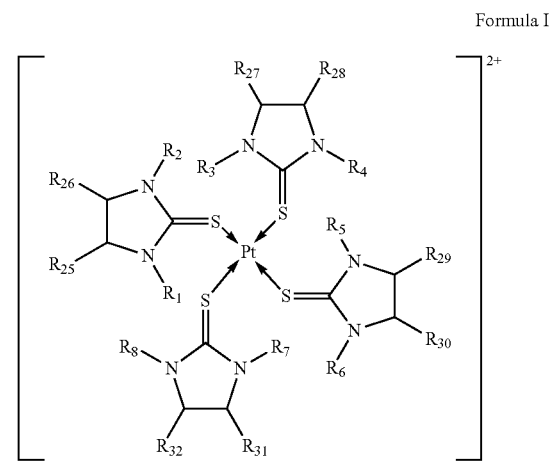

Formula I or a pharmaceutically acceptable salt, tautomer, ester, solvate or prodrug thereof;

wherein:

$R_1$, $R_3$, $R_5$, and $R_7$ are each independently a hydrogen atom, and $R_2$, $R_4$, $R_6$, and $R_8$ are each independently a $C_1$-$C_3$ alkyl group, and $R_{25}$-$R_{31}$ are each independently a hydrogen atom, a halogen atom, an optionally substituted $C_1$-$C_8$ alkyl group, an optionally substituted $C_1$-$C_8$ alkoxy group, an optionally substituted $C_2$-$C_8$ alkenyl group or an optionally substituted $C_2$-$C_8$ alkynyl group.

2. The platinum(II) complex of claim 1, wherein $R_2$, $R_4$, $R_6$, and $R_8$, are each a methyl group, an ethyl group, a propyl group or an isopropyl group; and $R_{25}$-$R_{31}$ are each a hydrogen atom.

3. The platinum(II) complex of claim 1, further comprising one or more pharmaceutically acceptable anions.

4. The platinum(II) complex of claim 2, wherein the one or more pharmaceutically acceptable anions are chloride and nitrate.

5. A pharmaceutical composition, comprising:

the platinum(II) complex of claim 1 or a pharmaceutically acceptable salt, tautomer, ester, solvate or prodrug thereof; and one or more pharmaceutically acceptable carriers.

6. The pharmaceutical composition of claim 5, further comprising one or more other active pharmaceutical agents.

7. The pharmaceutical composition of claim 5, further comprising one or more non-active ingredients.

* * * * *